(12) United States Patent
Hasui et al.

(10) Patent No.: US 11,447,488 B2
(45) Date of Patent: Sep. 20, 2022

(54) HETEROCYCLIC COMPOUNDS

(71) Applicant: Takeda Pharmaceutical Company Limited, Osaka (JP)

(72) Inventors: Tomoaki Hasui, Kanagawa (JP); Shinji Nakamura, Kanagawa (JP); Satoshi Mikami, Kanagawa (JP); Tohru Yamashita, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 78 days.

(21) Appl. No.: 16/753,630

(22) PCT Filed: Oct. 4, 2018

(86) PCT No.: PCT/JP2018/037283
§ 371 (c)(1),
(2) Date: Apr. 3, 2020

(87) PCT Pub. No.: WO2019/070044
PCT Pub. Date: Apr. 11, 2019

(65) Prior Publication Data
US 2020/0247801 A1    Aug. 6, 2020

(30) Foreign Application Priority Data

Oct. 6, 2017  (JP) .............. JP2017-195906

(51) Int. Cl.
*C07D 471/04* (2006.01)
*C07D 407/12* (2006.01)
*C07D 413/10* (2006.01)
*C07D 413/14* (2006.01)

(52) U.S. Cl.
CPC ......... *C07D 471/04* (2013.01); *C07D 407/12* (2013.01); *C07D 413/10* (2013.01); *C07D 413/14* (2013.01)

(58) Field of Classification Search
CPC ................................. C07D 471/04
USPC .................................. 514/210.18
See application file for complete search history.

(56) References Cited

U.S. PATENT DOCUMENTS

| | | |
|---|---|---|
| 2010/0041891 A1 | 2/2010 | Setoh et al. |
| 2011/0118236 A1 | 5/2011 | Mochizuki et al. |
| 2012/0077799 A1 | 3/2012 | Kori et al. |
| 2013/0184266 A1 | 7/2013 | Kori et al. |
| 2013/0190291 A1 | 7/2013 | Kori et al. |
| 2014/0024650 A1 | 1/2014 | Fukumoto et al. |
| 2014/0080817 A1 | 3/2014 | Kori et al. |
| 2015/0051197 A1 | 2/2015 | Toyofuki et al. |
| 2015/0073137 A1 | 3/2015 | Kori et al. |
| 2015/0353578 A1 | 12/2015 | Kori et al. |
| 2016/0280671 A1 | 9/2016 | Duggan |
| 2017/0022222 A1 | 1/2017 | Kori et al. |
| 2018/0118683 A1 | 5/2018 | Ameriks et al. |
| 2018/0118740 A1 | 5/2018 | Ameriks et al. |
| 2018/0118751 A1 | 5/2018 | Ameriks et al. |
| 2018/0162875 A1 | 6/2018 | Kori et al. |
| 2018/0179190 A1 | 6/2018 | Bennett et al. |
| 2018/0244656 A1 | 8/2018 | Bennett et al. |
| 2019/0092735 A1 | 3/2019 | Ameriks et al. |
| 2019/0144432 A1 | 5/2019 | Bennett et al. |
| 2019/0263832 A1 | 8/2019 | Kori et al. |

FOREIGN PATENT DOCUMENTS

| | | |
|---|---|---|
| WO | WO 2007/040438 A2 | 4/2007 |
| WO | WO-2009/119088 A1 | 10/2009 |
| WO | WO-2010/140339 A1 | 12/2010 |
| WO | WO-2011/036885 A1 | 3/2011 |
| WO | WO-2011/036889 A1 | 3/2011 |
| WO | WO-2012/020848 A1 | 2/2012 |
| WO | WO-2012/133607 A1 | 10/2012 |
| WO | WO-2012/137982 A2 | 10/2012 |
| WO | WO-2013/118845 A1 | 8/2013 |
| WO | WO-2014/092104 A1 | 6/2014 |

(Continued)

OTHER PUBLICATIONS

Baudry et al., "Ampakines promote spine actin polymerization, long-term potentiation, and learning in a mouse model of Angelman syndrome," Neurobiology of Disease, 2012, 47:210-215.

(Continued)

*Primary Examiner* — Kahsay Habte
(74) *Attorney, Agent, or Firm* — Finnegan, Henderson, Farabow, Garrett & Dünner, LLP

(57) ABSTRACT

The present invention aims to provide a heterocyclic compound having an AMPA receptor potentiator effect, which is expected to be useful as an agent for the prophylaxis or treatment of depression, Alzheimer's disease, schizophrenia, attention deficit hyperactivity disorder (ADHD) and the like.

The present invention relates to a compound represented by the formula (I):

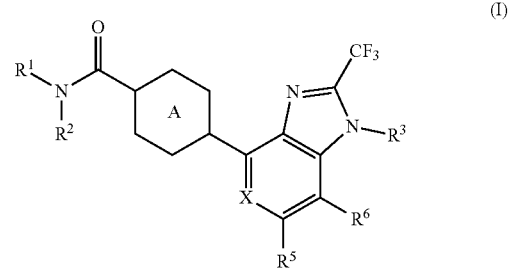

wherein each symbol is as described in the specification, or a salt thereof.

9 Claims, No Drawings
Specification includes a Sequence Listing.

(56) References Cited

FOREIGN PATENT DOCUMENTS

| WO | WO-2015/039172 A1 | 3/2015 |
|---|---|---|
| WO | WO-2016/176449 A1 | 11/2016 |
| WO | WO-2016/176457 A1 | 11/2016 |
| WO | WO-2016/176460 A1 | 11/2016 |
| WO | WO-2016/176463 A1 | 11/2016 |
| WO | WO-2016/206101 A1 | 12/2016 |
| WO | WO-2016/210234 A1 | 12/2016 |

OTHER PUBLICATIONS

Bettler et al., "Review: Neurotransmitter Receptors II AMPA and Kainate Receptors," Neuropharmacology, 1995, 34(2):123-139.

Bowie, Derek, "Ionotropic Glutamate Receptors & CNS Disorders," CNS & Neurological Disorders—Drug Targets, 2008, 7:129-143.

Clarkson et al., "AMPA Receptor-Induced Local Brain-Derived Neurotrophic Factor Signaling Mediates Motor Recovery after Stroke," Journal of Neuroscience, Mar. 9, 2011, 31(1):3766-3775.

Dingledine et al., "The Glutamate Receptor Ion Channels," Pharmacological Reviews, 1999, 51(1):7-61.

Hamaguchi et al., "Addressing phototoxicity observed in a novel series of biaryl derivatives: Discovery of potent, selective and orally active phosphodiesterase 10A inhibitor ASP9436," Bioorganic & Medicinal Chemistry, 2015, 23(13):3351-3367.

Malinow et al., "AMPA Receptor Trafficking and Synaptic Plasticity," Annual Review of Neuroscience, 2002, 25:103-126.

Morrow et al., "Recent advances in positive allosteric modulators of the AMPA receptor," Current Opinion in Drug Discovery and Development, 2006, 9(5):571-579.

Muddashetty et al. "Dysregulated Metabotropic Glutamate Receptor-Dependent Translation of AMPA Receptor and Postsynaptic Density-95 mRNAs at Synapses in a Mouse Model of Fragile X Syndrome," Journal of Neuroscience, May 16, 2007, 27(20):5338-5348.

Ogier et al., "Brain-Derived Neurotrophic Factor Expression and Respiratory Function Improve after Ampakine Treatment in a Mouse Model of Rett Syndrome," Journal of Neuroscience, Oct. 3, 2007, 27(40):10912-10917.

Wall et al., "Evaluation of N-(phenylmethyl)-4-[5-phenylmethyl)-4,5,6,7-tetrahydro-1H-imidazo[4,5-c]pyridine-4-yl]benzamide inhibitors of *Mycobacterium tuberculosis* growth," Bioorganic & Medicinal Chemistry Letters, 2007, 17(10):2740-2744.

Wang et al., "Synaptic Transmission at the Cochlear Nucleus Endbulb Synapse During Age-Related Hearing Loss in Mice," Journal of Neurophysiology, 2005, 94:1814-1824.

Extended European Search Report for corresponding Application No. EP 18864009.8 dated Dec. 17, 2020.

SEQUENCE LISTING

<160> NUMBER OF SEQ ID NOS: 4

<210> SEQ ID NO 1
<211> LENGTH: 42
<212> TYPE: DNA
<213> ORGANISM: Artificial
<220> FEATURE:
<223> OTHER INFORMATION: Forward primer for GluR1 flip cDNA

<400> SEQUENCE: 1
actgaattcg ccaccatgca gcacattttt gccttcttct gc        42

<210> SEQ ID NO 2
<211> LENGTH: 32
<212> TYPE: DNA

```
<213> ORGANISM: Artificial
<220> FEATURE:
<223> OTHER INFORMATION: Reverse primer for GluR1 flip cDNA

<400> SEQUENCE: 2
ccgcggccgc ttacaatccc gtggctccca ag                           32

<210> SEQ ID NO 3
<211> LENGTH: 41
<212> TYPE: DNA
<213> ORGANISM: Artificial
<220> FEATURE:
<223> OTHER INFORMATION: Forward primer for stargazin cDNA

<400> SEQUENCE: 3
ggtctcgagg ccaccatggg gctgtttgat cgaggtgttc a                 41

<210> SEQ ID NO 4
<211> LENGTH: 40
<212> TYPE: DNA
<213> ORGANISM: Artificial
<220> FEATURE:
<223> OTHER INFORMATION: Reverse primer for stargazin cDNA

<400> SEQUENCE: 4
gttggatcct tatacggggg tggtccggcg gttggctgtg                   40
```

HETEROCYCLIC COMPOUNDS

TECHNICAL FIELD

The present invention relates to a heterocyclic compound, particularly a heterocyclic compound having an AMPA (α-amino-3-hydroxy-5-methyl-4-isoxazolepropionic acid) receptor potentiator effect, which is expected to be useful as an agent for the prophylaxis or treatment of depression, Alzheimer's disease, schizophrenia, attention deficit hyperactivity disorder (ADHD) and the like.

BACKGROUND OF THE INVENTION

Glutamic acid is an excitatory neurotransmitter most abundantly present in the central nervous system of mammals. Glutamic acid plays an important role in the cognition, mood and control of motor function, and the neurotransmission thereof becomes unstable in psychiatric diseases and neuropathy. Glutamic acid receptors are classified into ion ligand-gated ion channel and G protein conjugated-type receptor, and the ligand-gated ion channel is further classified into α-amino-3-hydroxy-5-methyl-4-isoxazolepropionic acid (AMPA) receptor, N-methyl-D-aspartic acid (NMDA) receptor and kainic acid (KA) receptor (Non-patent Document 1).

AMPA receptor is one kind of receptor for excitatory neurotransmitter glutamic acid, and was named based on selective activation of the receptor by AMPA. AMPA receptor consists of 4 subunits (GluR1, GluR2, GluR3, GluR4). Each subunit contains flip type and flop type splicing variants. In the living body, AMPA receptor forms a homogeneous or heterogeneous tetramer consisting of such subunits. It has been reported that the physiological property of AMPA receptor varies depending on the subunits constituting the receptor (Non-patent Documents 1, 2 and 3).

The importance of AMPA receptor in brain physiology is well known, and a compound having an AMPA receptor potentiator effect is expected to be useful as an agent for the prophylaxis or treatment of psychiatric diseases, neurodegenerative disease, memory disorders, sleep disorder, genetic diseases associated with psychiatric disorders and cognitive impairment, stroke, hearing loss and the like (Non-patent Documents 4 to 10).

As a heterocyclic compound, the following compounds are disclosed.

(1) Patent Document 1 discloses a compound represented by the following formula:

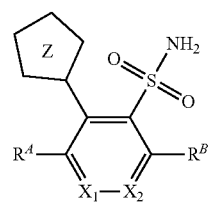

(I)

wherein each symbol is as defined in the document, which is a metallo-P-lactamase inhibitor and is useful as an antimicrobial agent and the like.

(2) Patent Document 2 discloses a compound represented by the following formula:

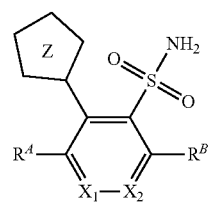

(I)

wherein each symbol is as defined in the document, which is a metallo-P-lactamase inhibitor and is useful as an antimicrobial agent and the like.

(3) Patent Document 3 discloses a compound represented by the following formula:

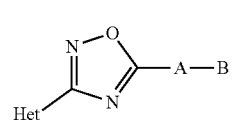

(1)

wherein each symbol is as defined in the document, which is a serotonin receptor agonist and is useful for Alzheimer-type dementia, depression, schizophrenia and the like.

(4) Non-Patent Document 11 discloses a compound represented by the following formula:

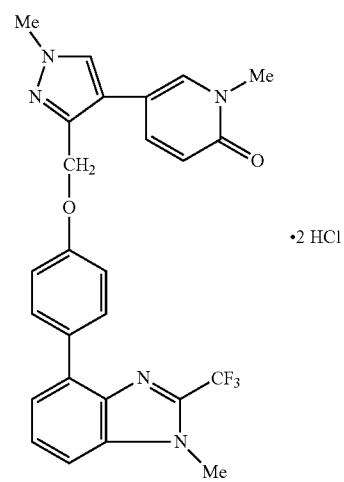 [SMILES: Cn1cc(-c2ccc(=O)n(C)c2)c(COc2ccc(-c3cccc4c3nc(C(F)(F)F)n4C)cc2)n1]

which is a PDE10A inhibitor and is useful for schizophrenia and the like.

(5) Patent Document 4 discloses a compound represented by the following formula:

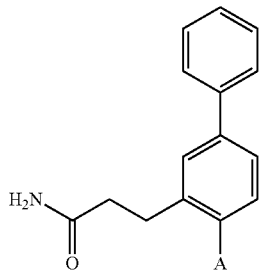

wherein each symbol is as defined in the document, which is useful for hypertension, fibrosis and the like.

(6) Patent Document 5 discloses a compound represented by the following formula:

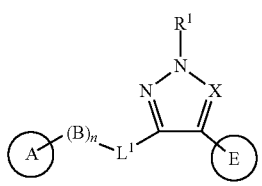
(I)

wherein each symbol is as defined in the document, which is a PDE10A inhibitor and is useful for schizophrenia, anxiety, Huntington's disease, drug dependence, cognitive impairment caused by Alzheimer's disease and peripheral symptoms thereof, and the like.

Moreover, as a heterocyclic compound having an AMPA receptor potentiator effect, the following compounds are disclosed.

(7) Patent Document 6 discloses a compound represented by the following formula:

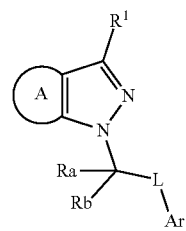

wherein each symbol is as defined in the document.

(8) Patent Document 7 discloses a compound represented by the following formula:

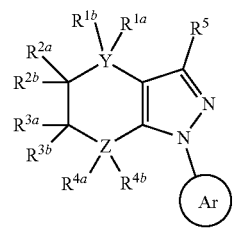

wherein each symbol is as defined in the document.

(9) Patent Document 8 discloses a compound represented by the following formula:

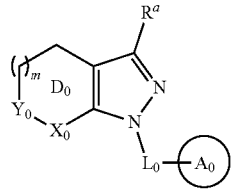

wherein each symbol is as defined in the document.

(10) Patent Document 9 discloses a compound represented by the following formula:

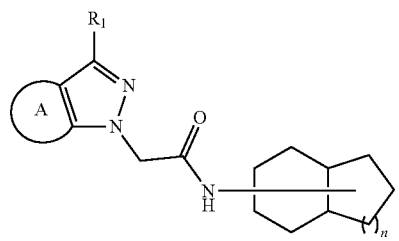

wherein each symbol is as defined in the document.

(11) Patent Document 10 discloses a compound represented by the following formula:

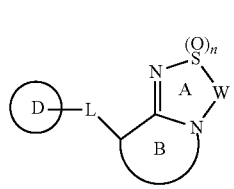
(I)

wherein each symbol is as defined in the document.

(12) Patent Document 11 discloses a compound represented by the following formula:

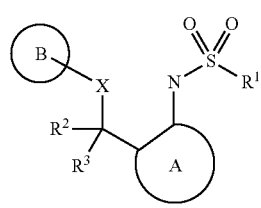
(I)

wherein each symbol is as defined in the document.

(13) Patent Document 12 discloses a compound represented by the following formula:

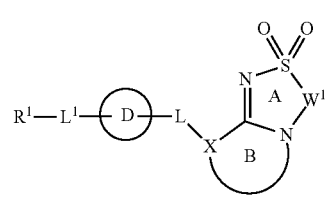
(I)

wherein each symbol is as defined in the document.

DOCUMENT LIST

Patent Document

Patent Document 1: WO 2016/210234
Patent Document 2: WO 2016/206101
Patent Document 3: WO 2014/092104
Patent Document 4: WO 2015/039172
Patent Document 5: WO 2012/133607
Patent Document 6: WO 2009/119088
Patent Document 7: WO 2010/140339
Patent Document 8: WO 2011/036889
Patent Document 9: WO 2011/036885
Patent Document 10: WO 2012/020848
Patent Document 11: WO 2012/137982
Patent Document 12: WO 2013/118845

Non-Patent Document

Non-Patent Document 1: Pharmacological Reviews, Vol. 51, p. 7-61, 1999
Non-Patent Document 2: Neuropharmacology, Vol. 34, p. 123-139, 1995
Non-Patent Document 3: Annual Review of Neuroscience, Vol. 25, p. 103-126, 2002
Non-Patent Document 4: CNS & Neurological Disorders-Drug Targets, Vol. 7, p. 129-143, 2008
Non-Patent Document 5: Current Opinion in Drug Discovery and Development, Vol. 9, p. 571-579, 2006
Non-Patent Document 6: Journal of Neuroscience, Vol. 27, p. 10912-10917, 2007
Non-Patent Document 7: Journal of Neuroscience, Vol. 27, p. 5338-5348, 2007
Non-Patent Document 8: Neurobiology of Disease, Vol. 47, p. 210-215, 2012
Non-Patent Document 9: Journal of Neuroscience, Vol. 31, p. 3766-3775, 2011
Non-Patent Document 10: Journal of Neurophysiology, Vol. 94, p. 1814-1824, 2005
Non-Patent Document 11: Bioorganic Medicinal Chemistry, Vol. 23(13), p. 3351-67

SUMMARY OF THE INVENTION

Problems to be Solved by the Invention

The present invention aims to provide a heterocyclic compound having an AMPA receptor potentiator effect, which is expected to be useful as an agent for the prophylaxis or treatment of depression, Alzheimer's disease, schizophrenia, attention deficit hyperactivity disorder (ADHD) and the like (AMPA receptor potentiator; AMPA receptor potentiator is sometimes also referred to as AMPA receptor positive modulator, AMPAkine, AMPA receptor allosteric modulator, AMPA receptor positive allosteric modulator or positive allosteric modulator of AMPA receptor).

Means of Solving the Problems

The present inventors have found that a compound represented by the following formula (I) or a salt thereof (in the present specification, sometimes to be referred to as compound (I) or simply as the compound of the present invention) may have an AMPA receptor potentiator effect, and conducted further studies, which resulted in the completion of the present invention. In this specification, compound (I) and a prodrug thereof are also sometimes collectively referred to as the compound of the present invention.

Accordingly, the present invention provides the following.

[1] A compound represented by the formula (I):

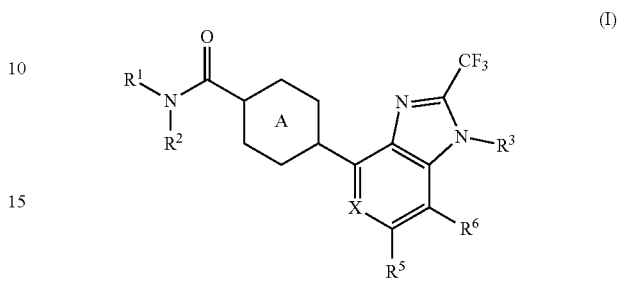

wherein
$R^1$ and $R^2$ are each independently a hydrogen atom or a substituent, or $R^1$ and $R^2$ are bonded to each other to form, together with the adjacent nitrogen atom, an optionally further substituted non-aromatic nitrogen-containing heterocycle,
$R^3$ is an optionally substituted $C_{1-6}$ alkyl group,
X is $CR^4$ or N,
$R^4$, $R^5$ and $R^6$ are each independently a hydrogen atom, a halogen atom, an optionally substituted $C_{1-6}$ alkyl group or an optionally substituted $C_{1-6}$ alkoxy group, and
Ring A is a 6-membered aromatic ring optionally further substituted by 1 to 4 substituents selected from (i) a halogen atom, (ii) a $C_{1-6}$ alkyl group and (iii) a $C_{1-6}$ alkoxy group, or a salt thereof.

[2]
The compound or salt of the above-mentioned [1], wherein
$R^1$ and $R^2$ are each independently
(1) a hydrogen atom,
(2) a $C_{1-6}$ alkyl group optionally substituted by 1 to 3 substituents selected from
   (a) a cyano group, and
   (b) a $C_{3-10}$ cycloalkyl group, or
(3) a 3- to 14-membered non-aromatic heterocyclic group, or
$R^1$ and $R^2$ are bonded to each other to form, together with the adjacent nitrogen atom, a 3- to 14-membered non-aromatic nitrogen-containing heterocycle optionally further substituted by 1 to 3 substituents selected from
   (a) a halogen atom,
   (b) a $C_{1-6}$ alkyl group optionally substituted by 1 to 3 halogen atoms, and
   (c) a $C_{1-6}$ alkoxy group;
$R^3$ is a $C_{1-6}$ alkyl group optionally substituted by 1 to 3 substituents selected from
   (a) a halogen atom,
   (b) a cyano group, and
   (c) a $C_{1-6}$ alkoxy group;
X is $CR^4$ or N;
$R^4$ is
(1) a hydrogen atom,
(2) a halogen atom, or
(3) a $C_{1-6}$ alkyl group;
$R^5$ is
(1) a hydrogen atom, or
(2) a $C_{1-6}$ alkyl group;
$R^6$ is a hydrogen atom; and Ring A is
(1) a benzene ring optionally further substituted by 1 to 4 substituents selected from (i) a halogen atom, and (ii) a $C_{1-6}$ alkoxy group, or
(2) a pyridine ring optionally further substituted by 1 to 4 halogen atoms.

[3]

The compound or salt of the above-mentioned [1], wherein
$R^1$ and $R^2$ are each independently
(1) a hydrogen atom,
(2) a $C_{1-6}$ alkyl group optionally substituted by 1 to 3 substituents selected from
    (a) a cyano group, and
    (b) a $C_{3-6}$ cycloalkyl group, or
(3) a tetrahydropyranyl group, or
$R^1$ and $R^2$ are bonded to each other to form, together with the adjacent nitrogen atom,
(1) a morpholine ring optionally further substituted by 1 to 3 substituents selected from
    (a) a halogen atom, and
    (b) a $C_{1-6}$ alkyl group optionally substituted by 1 to 3 halogen atoms,
(2) an oxazepane ring optionally further substituted by 1 to 3 halogen atoms,
(3) an azetidine ring optionally further substituted by 1 to 3 halogen atoms,
(4) a pyrrolidine ring optionally further substituted by 1 to 3 $C_{1-6}$ alkoxy groups,
(5) a piperidine ring optionally further substituted by 1 to 3 $C_{1-6}$ alkoxy groups, or
(6) a 5-oxa-8-azaspiro[2.6]nonane ring;
$R^3$ is a $C_{1-6}$ alkyl group optionally substituted by 1 to 3 substituents selected from
    (a) a halogen atom,
    (b) a cyano group, and
    (c) a $C_{1-6}$ alkoxy group;
X is $CR^4$ or N;
$R^4$ is
(1) a hydrogen atom,
(2) a halogen atom, or
(3) a $C_{1-6}$ alkyl group;
$R^5$ is
(1) a hydrogen atom, or
(2) a $C_{1-6}$ alkyl group;
$R^6$ is a hydrogen atom; and
Ring A is
(1) a benzene ring optionally further substituted by 1 to 4 substituents selected from (i) a halogen atom, and (ii) a $C_{1-6}$ alkoxy group, or
(2) a pyridine ring optionally further substituted by 1 to 4 halogen atoms.

[4]

The compound or salt of the above-mentioned [1], wherein
$R^1$ and $R^2$ are bonded to each other to form, together with the adjacent nitrogen atom,
(1) a morpholine ring, or
(2) an oxazepane ring optionally further substituted by 1 to 3 halogen atoms;
$R^3$ is a $C_{1-6}$ alkyl group substituted by 1 to 3 halogen atoms;
X is CH or N;
$R^5$ is a hydrogen atom;
$R^6$ is a hydrogen atom; and
Ring A is
(1) a benzene ring optionally further substituted by 1 or 2 halogen atoms, or
(2) a pyridine ring optionally further substituted by 1 or 2 halogen atoms.

[5]

The compound or salt of the above-mentioned [1], wherein
$R^1$ and $R^2$ are bonded to each other to form, together with the adjacent nitrogen atom,
(1) a morpholine ring, or
(2) an oxazepane ring;
$R^3$ is a $C_{1-6}$ alkyl group substituted by two halogen atoms;
X is CH or N;
$R^5$ is a hydrogen atom;
$R^6$ is a hydrogen atom; and
Ring A is
(1) a benzene ring optionally further substituted by one halogen atom, or
(2) a pyridine ring optionally further substituted by one halogen atom.

[6] (4-(1-(2,2-difluoroethyl)-2-(trifluoromethyl)-1H-imidazo[4,5-c]pyridin-4-yl)-2-fluorophenyl)(morpholin-4-yl)methanone, or a salt thereof.

[7] (4-(1-(2,2-difluoroethyl)-2-(trifluoromethyl)-1H-imidazo[4,5-c]pyridin-4-yl)-2-fluorophenyl)(1,4-oxazepan-4-yl)methanone, or a salt thereof.

[8] (5-(1-(2,2-difluoroethyl)-2-(trifluoromethyl)-1H-benzimidazol-4-yl)-3-fluoropyridin-2-yl)(morpholin-4-yl)methanone, or a salt thereof.

[9] A medicament comprising the compound or salt of any of the above-mentioned [1] to [8].

[10] The medicament of the above-mentioned [9], which is an AMPA receptor potentiator.

[11] The medicament of the above-mentioned [9], which is an agent for the prophylaxis or treatment of depression, Alzheimer's disease, schizophrenia or attention deficit hyperactivity disorder.

[12] The compound or salt of any of the above-mentioned [1] to [8] for use in the prophylaxis or treatment of depression, Alzheimer's disease, schizophrenia or attention deficit hyperactivity disorder.

[13] A method of enhancing AMPA receptor function in a mammal, which comprises administering an effective amount of the compound or salt of any of the above-mentioned [1] to [8] to the mammal.

[14] A method for the prophylaxis or treatment of depression, schizophrenia, Alzheimer's disease or attention deficit hyperactivity disorder in a mammal, which comprises administering an effective amount of the compound or salt of any of the above-mentioned [1] to [8] to the mammal.

[15] Use of the compound or salt of any of the above-mentioned [1] to [8] for the manufacture of an agent for the prophylaxis or treatment of depression, Alzheimer's disease, schizophrenia or attention deficit hyperactivity disorder.

Effect of the Invention

According to the present invention, a useful compound having an AMPA receptor potentiator effect, which is expected to be useful as an agent for the prophylaxis or treatment of depression, Alzheimer's disease, schizophrenia, attention deficit hyperactivity disorder (ADHD) and the like, can be provided.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl) amino group (e.g., N-acetyl-N-methylamino) and a ($C_{1-6}$ alkyl)($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A". Preferable examples of the optionally substituted silyl group include a tri-$C_{1-6}$ alkylsilyl group (e.g., trimethylsilyl, tert-butyl(dimethyl)silyl).

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho [2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

The definition of each symbol in the formula (I) is explained below.

$R^1$ and $R^2$ are each independently a hydrogen atom or a substituent, or $R^1$ and $R^2$ are bonded to each other to form, together with the adjacent nitrogen atom, an optionally further substituted non-aromatic nitrogen-containing heterocycle.

The "substituent" represented by $R^1$ or $R^2$ is preferably
(1) an optionally substituted $C_{1-6}$ alkyl group (e.g., methyl, ethyl), or
(2) an optionally substituted 3- to 14-membered non-aromatic heterocyclic group (preferably a 3- to 8-membered monocyclic non-aromatic heterocyclic group (e.g., tetrahydropyranyl)).

The "substituent" represented by $R^1$ or $R^2$ is more preferably
(1) a $C_{1-6}$ alkyl group (e.g., methyl, ethyl) optionally substituted by 1 to 3 substituents selected from
  (a) a cyano group, and
  (b) a $C_{3-10}$ cycloalkyl group (e.g., cyclopropyl), or
(2) a 3- to 14-membered non-aromatic heterocyclic group (preferably a 3- to 8-membered monocyclic non-aromatic heterocyclic group (e.g., tetrahydropyranyl)).

Examples of the "non-aromatic nitrogen-containing heterocycle" of the "optionally further substituted non-aromatic nitrogen-containing heterocycle" formed by $R^1$ and $R^2$ bonded to each other, together with the adjacent nitrogen atom, include a non-aromatic heterocycle containing at least one nitrogen atom as a ring-constituting atom, from among the "non-aromatic heterocycle".

The "non-aromatic nitrogen-containing heterocycle" includes a 6- to 9-membered nitrogen-containing spiro ring (e.g., 5-oxa-8-azaspiro[2.6]nonane).

Preferable examples of the "non-aromatic nitrogen-containing heterocycle" include a 3- to 14-membered monocyclic non-aromatic nitrogen-containing heterocycle (preferably a 3- to 8-membered monocyclic non-aromatic nitrogen-containing heterocycle (e.g., azetidine, pyrrolidine, piperidine, morpholine, oxazepane (e.g., 1,4-oxazepane)), a 6- to 9-membered nitrogen-containing spiro ring (e.g., 5-oxa-8-azaspiro[2.6]nonane)) and the like.

The "non-aromatic nitrogen-containing heterocycle" is preferably a 3- to 8-membered monocyclic non-aromatic nitrogen-containing heterocycle (e.g., azetidine, pyrrolidine, piperidine, morpholine, oxazepane (e.g., 1,4-oxazepane)), or a 6- to 9-membered nitrogen-containing spiro ring (e.g., 5-oxa-8-azaspiro[2.6]nonane).

The "non-aromatic nitrogen-containing heterocycle" is more preferably a morpholine ring, an oxazepane ring (preferably 1,4-oxazepane), an azetidine ring, a pyrrolidine ring, a piperidine ring or a 5-oxa-8-azaspiro[2.6]nonane ring.

The "non-aromatic nitrogen-containing heterocycle" is further more preferably a morpholine ring or an oxazepane ring (preferably 1,4-oxazepane).

The "non-aromatic nitrogen-containing heterocycle" is particularly preferably a morpholine ring.

The "non-aromatic nitrogen-containing heterocycle" of the "optionally further substituted non-aromatic nitrogen-containing heterocycle" formed by $R^1$ and $R^2$ bonded to each other, together with the adjacent nitrogen atom, is optionally further substituted, at substitutable position(s), by substituent(s) selected from the above-mentioned Substituent Group A. The number of the substituents is, for example, 1 to 3. When the number of the substituents is 2 or more, the respective substituents may be the same or different. In addition, the Substituent Group A is optionally further substituted by substituent(s) selected from the above-mentioned Substituent Group A. The number of the substituents is, for example, 1 to 3. When the number of the substituents is 2 or more, the respective substituents may be the same or different.

Preferable examples of the "substituent" of the "non-aromatic nitrogen-containing heterocycle" include
  (a) a halogen atom (e.g., a fluorine atom),
  (b) a $C_{1-6}$ alkyl group (e.g., methyl) optionally substituted by 1 to 3 halogen atoms (e.g., a fluorine atom), and
  (c) a $C_{1-6}$ alkoxy group (e.g., methoxy).

$R^1$ and $R^2$ are preferably each independently
(1) a hydrogen atom,
(2) an optionally substituted $C_{1-6}$ alkyl group (e.g., methyl, ethyl), or
(3) an optionally substituted 3- to 14-membered non-aromatic heterocyclic group (preferably a 3- to 8-membered monocyclic non-aromatic heterocyclic group (e.g., tetrahydropyranyl)), or
$R^1$ and $R^2$ are bonded to each other to form, together with the adjacent nitrogen atom, an optionally further substituted 3- to 14-membered non-aromatic nitrogen-containing heterocycle (preferably a 3- to 8-membered monocyclic non-aromatic nitrogen-containing heterocycle (e.g., azetidine, pyrrolidine, piperidine, morpholine, oxazepane (e.g., 1,4-oxazepane)), a 6- to 9-membered nitrogen-containing spiro ring (e.g., 5-oxa-8-azaspiro[2.6]nonane)).

$R^1$ and $R^2$ are more preferably each independently
(1) a hydrogen atom,
(2) a $C_{1-6}$ alkyl group (e.g., methyl, ethyl) optionally substituted by 1 to 3 substituents selected from
  (a) a cyano group, and
  (b) a $C_{3-10}$ cycloalkyl group (e.g., cyclopropyl), or
(3) a 3- to 14-membered non-aromatic heterocyclic group (preferably a 3- to 8-membered monocyclic non-aromatic heterocyclic group (e.g., tetrahydropyranyl)), or
$R^1$ and $R^2$ are bonded to each other to form, together with the adjacent nitrogen atom, a 3- to 14-membered non-aromatic nitrogen-containing heterocycle (preferably a 3- to 8-membered monocyclic non-aromatic nitrogen-containing heterocycle (e.g., azetidine, pyrrolidine, piperidine, morpholine, oxazepane (e.g., 1,4-oxazepane)), a 6- to 9-membered nitrogen-containing spiro ring (e.g., 5-oxa-8-azaspiro[2.6]nonane)) optionally further substituted by 1 to 3 substituents selected from
  (a) a halogen atom (e.g., a fluorine atom),
  (b) a $C_{1-6}$ alkyl group (e.g., methyl) optionally substituted by 1 to 3 halogen atoms (e.g., a fluorine atom), and
  (c) a $C_{1-6}$ alkoxy group (e.g., methoxy).

$R^1$ and $R^2$ are further more preferably each independently
(1) a hydrogen atom,
(2) a $C_{1-6}$ alkyl group (e.g., methyl, ethyl) optionally substituted by 1 to 3 substituents selected from
  (a) a cyano group, and
  (b) a $C_{3-6}$ cycloalkyl group (e.g., cyclopropyl), or
(3) a 3- to 8-membered monocyclic non-aromatic heterocyclic group (e.g., tetrahydropyranyl), or
$R^1$ and $R^2$ are bonded to each other to form, together with the adjacent nitrogen atom, a 3- to 8-membered monocyclic non-aromatic nitrogen-containing heterocycle (e.g., azetidine, pyrrolidine, piperidine, morpholine, oxazepane (e.g., 1,4-oxazepane)), or a 6- to 9-membered nitrogen-containing spiro ring (e.g., 5-oxa-8-azaspiro[2.6]nonane), each optionally further substituted by 1 to 3 substituents selected from
  (a) a halogen atom (e.g., a fluorine atom),
  (b) a $C_{1-6}$ alkyl group (e.g., methyl) optionally substituted by 1 to 3 halogen atoms (e.g., a fluorine atom), and
  (c) a $C_{1-6}$ alkoxy group (e.g., methoxy).

$R^1$ and $R^2$ are still more preferably each independently
(1) a hydrogen atom,
(2) a $C_{1-6}$ alkyl group (e.g., methyl, ethyl) optionally substituted by 1 to 3 substituents selected from
  (a) a cyano group, and
  (b) a $C_{3-6}$ cycloalkyl group (e.g., cyclopropyl), or
(3) a tetrahydropyranyl group, or
$R^1$ and $R^2$ are bonded to each other to form, together with the adjacent nitrogen atom,
(1) a morpholine ring optionally further substituted by 1 to 3 substituents selected from
  (a) a halogen atom (e.g., a fluorine atom), and
  (b) a $C_{1-6}$ alkyl group (e.g., methyl) optionally substituted by 1 to 3 halogen atoms (e.g., a fluorine atom),
(2) an oxazepane ring (e.g., 1,4-oxazepane) optionally further substituted by 1 to 3 halogen atoms (e.g., a fluorine atom),
(3) an azetidine ring optionally further substituted by 1 to 3 halogen atoms (e.g., a fluorine atom),
(4) a pyrrolidine ring optionally further substituted by 1 to 3 $C_{1-6}$ alkoxy groups (e.g., methoxy),
(5) a piperidine ring optionally further substituted by 1 to 3 $C_{1-6}$ alkoxy groups (e.g., methoxy), or
(6) a 5-oxa-8-azaspiro[2.6]nonane ring.

$R^1$ and $R^2$ are even more preferably each independently
(1) a $C_{1-6}$ alkyl group (e.g., methyl, ethyl) optionally substituted by 1 to 3 cyano groups, or
(2) a tetrahydropyranyl group, or
$R^1$ and $R^2$ are bonded to each other to form, together with the adjacent nitrogen atom,
(1) a morpholine ring optionally further substituted by 1 to 3 $C_{1-6}$ alkyl groups (e.g., methyl) optionally substituted by 1 to 3 halogen atoms (e.g., a fluorine atom),
(2) an oxazepane ring (e.g., 1,4-oxazepane) optionally further substituted by 1 to 3 halogen atoms (e.g., a fluorine atom),
(3) an azetidine ring optionally further substituted by 1 to 3 halogen atoms (e.g., a fluorine atom), (4) a pyrrolidine ring optionally further substituted by 1 to 3 $C_{1-6}$ alkoxy groups (e.g., methoxy),
(5) a piperidine ring optionally further substituted by 1 to 3 $C_{1-6}$ alkoxy groups (e.g., methoxy), or
(6) a 5-oxa-8-azaspiro[2.6]nonane ring.

Even more preferably, $R^1$ and $R^2$ are bonded to each other to form, together with the adjacent nitrogen atom,
(1) a morpholine ring, or
(2) an oxazepane ring (e.g., 1,4-oxazepane) optionally further substituted by 1 to 3 halogen atoms (e.g., a fluorine atom).

Even more preferably, $R^1$ and $R^2$ are bonded to each other to form, together with the adjacent nitrogen atom,
(1) a morpholine ring, or
(2) an oxazepane ring (e.g., 1,4-oxazepane) further substituted by two halogen atoms (e.g., a fluorine atom).

Particularly preferably, $R^1$ and $R^2$ are bonded to each other to form, together with the adjacent nitrogen atom,
(1) a morpholine ring, or
(2) an oxazepane ring (e.g., 1,4-oxazepane).

$R^3$ is an optionally substituted $C_{1-6}$ alkyl group.

The "$C_{1-6}$ alkyl group" of the "optionally substituted $C_{1-6}$ alkyl group" represented by $R^3$ is optionally substituted, at substitutable position(s), by substituent(s) selected from the above-mentioned Substituent Group A. The number of the substituents is, for example, 1 to 3. When the number of the substituents is 2 or more, the respective substituents may be the same or different.

$R^3$ is preferably a $C_{1-6}$ alkyl group (e.g., methyl, ethyl, isopropyl) optionally substituted by 1 to 3 substituents selected from
(a) a halogen atom (e.g., a fluorine atom),
(b) a cyano group, and
(c) a $C_{1-6}$ alkoxy group (e.g., methoxy).

$R^3$ is more preferably a $C_{1-6}$ alkyl group (e.g., methyl, ethyl) optionally substituted by 1 to 3 (preferably 2) halogen atoms (e.g., a fluorine atom).

$R^3$ is further more preferably a $C_{1-6}$ alkyl group (e.g., ethyl) substituted by 1 to 3 (preferably 2) halogen atoms (e.g., a fluorine atom).

$R^3$ is particularly preferably a $C_{1-6}$ alkyl group (e.g., ethyl) substituted by two halogen atoms (e.g., a fluorine atom).

$R^4$, $R^5$ and $R^6$ are each independently a hydrogen atom, a halogen atom, an optionally substituted $C_{1-6}$ alkyl group or an optionally substituted $C_{1-6}$ alkoxy group.

The "$C_{1-6}$ alkyl group" of the "optionally substituted $C_{1-6}$ alkyl group" represented by $R^4$, $R^5$ or $R^6$ is optionally further substituted, at substitutable position(s), by substituent(s) selected from the above-mentioned Substituent Group A. The number of the substituents is, for example, 1 to 3. When the number of the substituents is 2 or more, the respective substituents may be the same or different.

The "$C_{1-6}$ alkoxy group" of the "optionally substituted $C_{1-6}$ alkoxy group" represented by $R^4$, $R^5$ or $R^6$ is optionally further substituted, at substitutable position(s), by substituent(s) selected from the above-mentioned Substituent Group A. The number of the substituents is, for example, 1 to 3. When the number of the substituents is 2 or more, the respective substituents may be the same or different.

$R^4$ is preferably
(1) a hydrogen atom,
(2) a halogen atom (e.g., a fluorine atom), or
(3) an optionally substituted $C_{1-6}$ alkyl group (e.g., methyl).

$R^4$ is more preferably
(1) a hydrogen atom,
(2) a halogen atom (e.g., a fluorine atom), or
(3) a $C_{1-6}$ alkyl group (e.g., methyl).

$R^4$ is further more preferably
(1) a hydrogen atom, or
(2) a halogen atom (e.g., a fluorine atom).

$R^4$ is particularly preferably a hydrogen atom.

$R^5$ is preferably
(1) a hydrogen atom, or
(2) an optionally substituted $C_{1-6}$ alkyl group (e.g., methyl).

$R^5$ is more preferably
(1) a hydrogen atom, or
(2) a $C_{1-6}$ alkyl group (e.g., methyl).

$R^5$ is particularly preferably a hydrogen atom.

$R^6$ is preferably a hydrogen atom.

X is $CR^4$ or N.

X is preferably CH, CF, $CCH_3$ or N.

X is more preferably CH, CF or N.

X is further more preferably CH or N.

X is particularly preferably CH.

Ring A is a 6-membered aromatic ring optionally further substituted by 1 to 4 substituents selected from (i) a halogen atom, (ii) a $C_{1-6}$ alkyl group and (iii) a $C_{1-6}$ alkoxy group.

Examples of the "6-membered aromatic ring" include a benzene ring, a pyridine ring, a pyrazine ring, a pyrimidine ring, a pyridazine ring and a triazine ring. The "6-membered aromatic ring" is preferably a benzene ring or a pyridine ring, particularly preferably a pyridine ring.

Ring A is preferably a 6-membered aromatic ring (e.g., benzene, pyridine) optionally further substituted by 1 to 4 (preferably 1 or 2) substituents selected from (i) a halogen atom (e.g., a fluorine atom) and (ii) a $C_{1-6}$ alkoxy group (e.g., methoxy).

Ring A is more preferably
(1) a benzene ring optionally further substituted by 1 to 4 (preferably 1 or 2) substituents selected from (i) a halogen atom (e.g., a fluorine atom) and (ii) a $C_{1-6}$ alkoxy group (e.g., methoxy), or
(2) a pyridine ring optionally further substituted by 1 to 4 (preferably 1 or 2) halogen atoms (e.g., a fluorine atom).

Ring A is further more preferably
(1) a benzene ring optionally further substituted by 1 or 2 halogen atoms (e.g., a fluorine atom), or
(2) a pyridine ring optionally further substituted by 1 or 2 halogen atoms (e.g., a fluorine atom).

Ring A is still more preferably,
(1) a benzene ring optionally further substituted by one halogen atom (e.g., a fluorine atom), or
(2) a pyridine ring optionally further substituted by one halogen atom (e.g., a fluorine atom).

Ring A is particularly preferably
(1) a benzene ring further substituted by one halogen atom (e.g., a fluorine atom), or
(2) a pyridine ring optionally further substituted by one halogen atom (e.g., a fluorine atom).

As another embodiment, Ring A is preferably a benzene ring or a pyridine ring, each optionally further substituted by 1 to 4 substituents selected from (i) a halogen atom, (ii) a $C_{1-6}$ alkyl group and (iii) a $C_{1-6}$ alkoxy group.

Preferable examples of compound (I) include the following compounds:
[Compound A]
Compound (I) wherein
$R^1$ and $R^2$ are each independently
(1) a hydrogen atom,
(2) an optionally substituted $C_{1-6}$ alkyl group (e.g., methyl, ethyl), or (3) an optionally substituted 3- to 14-membered non-aromatic heterocyclic group (preferably a 3- to 8-membered monocyclic non-aromatic heterocyclic group (e.g., tetrahydropyranyl)), or $R^1$ and $R^2$ are bonded to each other to form, together with the adjacent nitrogen atom, an optionally further substituted 3- to 14-membered non-aromatic nitrogen-containing heterocycle (preferably a 3- to 8-membered monocyclic non-aromatic nitrogen-containing heterocycle (e.g., azetidine, pyrrolidine, piperidine, morpholine, oxazepane (e.g., 1,4-oxazepane)), a 6- to 9-membered nitrogen-containing spiro ring (e.g., 5-oxa-8-azaspiro[2.6]nonane));

$R^3$ is an optionally substituted $C_{1-6}$ alkyl group (e.g., methyl, ethyl, isopropyl);

X is $CR^4$ or N;

$R^4$ is
(1) a hydrogen atom,
(2) a halogen atom (e.g., a fluorine atom), or
(3) an optionally substituted $C_{1-6}$ alkyl group (e.g., methyl);

$R^5$ is
(1) a hydrogen atom, or
(2) an optionally substituted $C_{1-6}$ alkyl group (e.g., methyl);

$R^6$ is a hydrogen atom; and

Ring A is a 6-membered aromatic ring (e.g., benzene, pyridine) optionally further substituted by 1 to 4 (preferably 1 or 2) substituents selected from (i) a halogen atom (e.g., a fluorine atom) and (ii) a $C_{1-6}$ alkoxy group (e.g., methoxy).

[Compound B]

Compound (I) wherein $R^1$ and $R^2$ are each independently
(1) a hydrogen atom,
(2) a $C_{1-6}$ alkyl group (e.g., methyl, ethyl) optionally substituted by 1 to 3 substituents selected from
  (a) a cyano group, and
  (b) a $C_{3-10}$ cycloalkyl group (e.g., cyclopropyl), or
(3) a 3- to 14-membered non-aromatic heterocyclic group (preferably a 3- to 8-membered monocyclic non-aromatic heterocyclic group (e.g., tetrahydropyranyl)), or $R^1$ and $R^2$ are bonded to each other to form, together with the adjacent nitrogen atom, a 3- to 14-membered non-aromatic nitrogen-containing heterocycle (preferably a 3- to 8-membered monocyclic non-aromatic nitrogen-containing heterocycle (e.g., azetidine, pyrrolidine, piperidine, morpholine, oxazepane (e.g., 1,4-oxazepane)), a 6- to 9-membered nitrogen-containing spiro ring (e.g., 5-oxa-8-azaspiro[2.6]nonane)) optionally further substituted by 1 to 3 substituents selected from
  (a) a halogen atom (e.g., a fluorine atom),
  (b) a $C_{1-6}$ alkyl group (e.g., methyl) optionally substituted by 1 to 3 halogen atoms (e.g., a fluorine atom), and
  (c) a $C_{1-6}$ alkoxy group (e.g., methoxy);

$R^3$ is a $C_{1-6}$ alkyl group (e.g., methyl, ethyl, isopropyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy);

X is $CR^4$ or N (preferably CH, CF, $CCH_3$ or N);

$R^4$ is
(1) a hydrogen atom,
(2) a halogen atom (e.g., a fluorine atom), or
(3) a $C_{1-6}$ alkyl group (e.g., methyl);

$R^5$ is
(1) a hydrogen atom, or
(2) a $C_{1-6}$ alkyl group (e.g., methyl);

$R^6$ is a hydrogen atom; and

Ring A is
(1) a benzene ring optionally further substituted by 1 to 4 (preferably 1 or 2) substituents selected from (i) a halogen atom (e.g., a fluorine atom) and (ii) a $C_{1-6}$ alkoxy group (e.g., methoxy), or
(2) a pyridine ring optionally further substituted by 1 to 4 (preferably 1 or 2) halogen atoms (e.g., a fluorine atom).

[Compound C]

[Compound B] wherein $R^1$ and $R^2$ are each independently
(1) a hydrogen atom,
(2) a $C_{1-6}$ alkyl group (e.g., methyl, ethyl) optionally substituted by 1 to 3 substituents selected from
  (a) a cyano group, and
  (b) a $C_{3-6}$ cycloalkyl group (e.g., cyclopropyl), or
(3) a 3- to 8-membered monocyclic non-aromatic heterocyclic group (e.g., tetrahydropyranyl), or $R^1$ and $R^2$ are bonded to each other to form, together with the adjacent nitrogen atom, a 3- to 8-membered monocyclic non-aromatic nitrogen-containing heterocycle (e.g., azetidine, pyrrolidine, piperidine, morpholine, oxazepane (e.g., 1,4-oxazepane)), or a 6- to 9-membered nitrogen-containing spiro ring (e.g., 5-oxa-8-azaspiro[2.6]nonane), each optionally further substituted by 1 to 3 substituents selected from
  (a) a halogen atom (e.g., a fluorine atom),
  (b) a $C_{1-6}$ alkyl group (e.g., methyl) optionally substituted by 1 to 3 halogen atoms (e.g., a fluorine atom), and
  (c) a $C_{1-6}$ alkoxy group (e.g., methoxy).

[Compound D]

[Compound B] wherein $R^1$ and $R^2$ are each independently
(1) a hydrogen atom,
(2) a $C_{1-6}$ alkyl group (e.g., methyl, ethyl) optionally substituted by 1 to 3 substituents selected from
  (a) a cyano group, and
  (b) a $C_{3-6}$ cycloalkyl group (e.g., cyclopropyl), or
(3) a tetrahydropyranyl group, or $R^1$ and $R^2$ are bonded to each other to form, together with the adjacent nitrogen atom,
(1) a morpholine ring optionally further substituted by 1 to 3 substituents selected from
  (a) a halogen atom (e.g., a fluorine atom), and
  (b) a $C_{1-6}$ alkyl group (e.g., methyl) optionally substituted by 1 to 3 halogen atoms (e.g., a fluorine atom),
(2) an oxazepane ring (e.g., 1,4-oxazepane) optionally further substituted by 1 to 3 halogen atoms (e.g., a fluorine atom),
(3) an azetidine ring optionally further substituted by 1 to 3 halogen atoms (e.g., a fluorine atom),
(4) a pyrrolidine ring optionally further substituted by 1 to 3 $C_{1-6}$ alkoxy groups (e.g., methoxy),
(5) a piperidine ring optionally further substituted by 1 to 3 $C_{1-6}$ alkoxy groups (e.g., methoxy), or
(6) a 5-oxa-8-azaspiro[2.6]nonane ring.

[Compound E]

Compound (I) wherein $R^1$ and $R^2$ are each independently
(1) a $C_{1-6}$ alkyl group (e.g., methyl, ethyl) optionally substituted by 1 to 3 cyano groups, or
(2) a tetrahydropyranyl group, or $R^1$ and $R^2$ are bonded to each other to form, together with the adjacent nitrogen atom,
(1) a morpholine ring optionally further substituted by 1 to 3 $C_{1-6}$ alkyl groups (e.g., methyl) optionally substituted by 1 to 3 halogen atoms (e.g., a fluorine atom),
(2) an oxazepane ring (e.g., 1,4-oxazepane) optionally further substituted by 1 to 3 halogen atoms (e.g., a fluorine atom), (3) an azetidine ring optionally further substituted by 1 to 3 halogen atoms (e.g., a fluorine atom),
(4) a pyrrolidine ring optionally further substituted by 1 to 3 $C_{1-6}$ alkoxy groups (e.g., methoxy),
(5) a piperidine ring optionally further substituted by 1 to 3 $C_{1-6}$ alkoxy groups (e.g., methoxy), or
(6) a 5-oxa-8-azaspiro[2.6]nonane ring;
$R^3$ is a $C_{1-6}$ alkyl group (e.g., methyl, ethyl) optionally substituted by 1 to 3 (preferably 2) halogen atoms (e.g., a fluorine atom);
X is $CR^4$ or N (preferably CH, CF or N);
$R^4$ is
(1) a hydrogen atom, or
(2) a halogen atom (e.g., a fluorine atom);
$R^5$ is
(1) a hydrogen atom, or
(2) a $C_{1-6}$ alkyl group (e.g., methyl);
$R^6$ is a hydrogen atom; and
Ring A is
(1) a benzene ring optionally further substituted by 1 or 2 halogen atoms (e.g., a fluorine atom), or
(2) a pyridine ring optionally further substituted by 1 or 2 halogen atoms (e.g., a fluorine atom).
[Compound F]
  Compound (I) wherein
$R^1$ and $R^2$ are bonded to each other to form, together with the adjacent nitrogen atom,
(1) a morpholine ring, or
(2) an oxazepane ring (e.g., 1,4-oxazepane) optionally further substituted by 1 to 3 halogen atoms (e.g., a fluorine atom);
$R^3$ is a $C_{1-6}$ alkyl group (e.g., ethyl) substituted by 1 to 3 (preferably 2) halogen atoms (e.g., a fluorine atom);
X is CH or N;
$R^5$ is a hydrogen atom;
$R^6$ is a hydrogen atom; and
Ring A is
(1) a benzene ring optionally further substituted by 1 or 2 halogen atoms (e.g., a fluorine atom), or
(2) a pyridine ring optionally further substituted by 1 or 2 halogen atoms (e.g., a fluorine atom).
[Compound G]
  [Compound F] wherein
$R^1$ and $R^2$ are bonded to each other to form, together with the adjacent nitrogen atom,
(1) a morpholine ring, or
(2) an oxazepane ring (e.g., 1,4-oxazepane) further substituted by two halogen atoms (e.g., a fluorine atom);
$R^3$ is a $C_{1-6}$ alkyl group (e.g., ethyl) substituted by two halogen atoms (e.g., a fluorine atom);
Ring A is
(1) a benzene ring further substituted by one halogen atom (e.g., a fluorine atom), or
(2) a pyridine ring optionally further substituted by one halogen atom (e.g., a fluorine atom).
[Compound H]
  [Compound F] wherein
$R^1$ and $R^2$ are bonded to each other to form, together with the adjacent nitrogen atom,
(1) a morpholine ring, or
(2) an oxazepane ring (e.g., 1,4-oxazepane);
$R^3$ is a $C_{1-6}$ alkyl group (e.g., ethyl) substituted by two halogen atoms (e.g., a fluorine atom); and
Ring A is
(1) a benzene ring optionally further substituted by one halogen atom (e.g., a fluorine atom), or
(2) a pyridine ring optionally further substituted by one halogen atom (e.g., a fluorine atom).
[Compound I]
(4-(1-(2,2-difluoroethyl)-2-(trifluoromethyl)-1H-imidazo[4,5-c]pyridin-4-yl)-2-fluorophenyl)(morpholin-4-yl)methanone, or a salt thereof.
(4-(1-(2,2-difluoroethyl)-2-(trifluoromethyl)-1H-imidazo[4,5-c]pyridin-4-yl)-2-fluorophenyl)(1,4-oxazepan-4-yl)methanone, or a salt thereof.
(5-(1-(2,2-difluoroethyl)-2-(trifluoromethyl)-1H-benzimidazol-4-yl)-3-fluoropyridin-2-yl)(morpholin-4-yl)methanone, or a salt thereof.

Specific examples of compound (I) include the compounds of Examples 1 to 59.

When compound (I) is a salt, it is preferably a pharmacologically acceptable salt, and examples of such salt include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like, alkaline earth metal salts such as calcium salt, magnesium salt and the like, aluminum salt, ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like. Preferable examples of the salt with acidic amino acid include salts with aspartic acid, glutamic acid and the like.

The production method of the compound of the present invention is explained below.

The raw material compound and reagent used and the compound obtained in each step in the following production method may be each in a form of a salt, and examples of such salt include those similar to the salts of compound (I) and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise 35 specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol, 2-methyl-2-butanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, N,N-diisopropylethylamine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is to reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide (WSC) hydrochloride and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Compound (I) can be produced from compound (1) according to the following method.

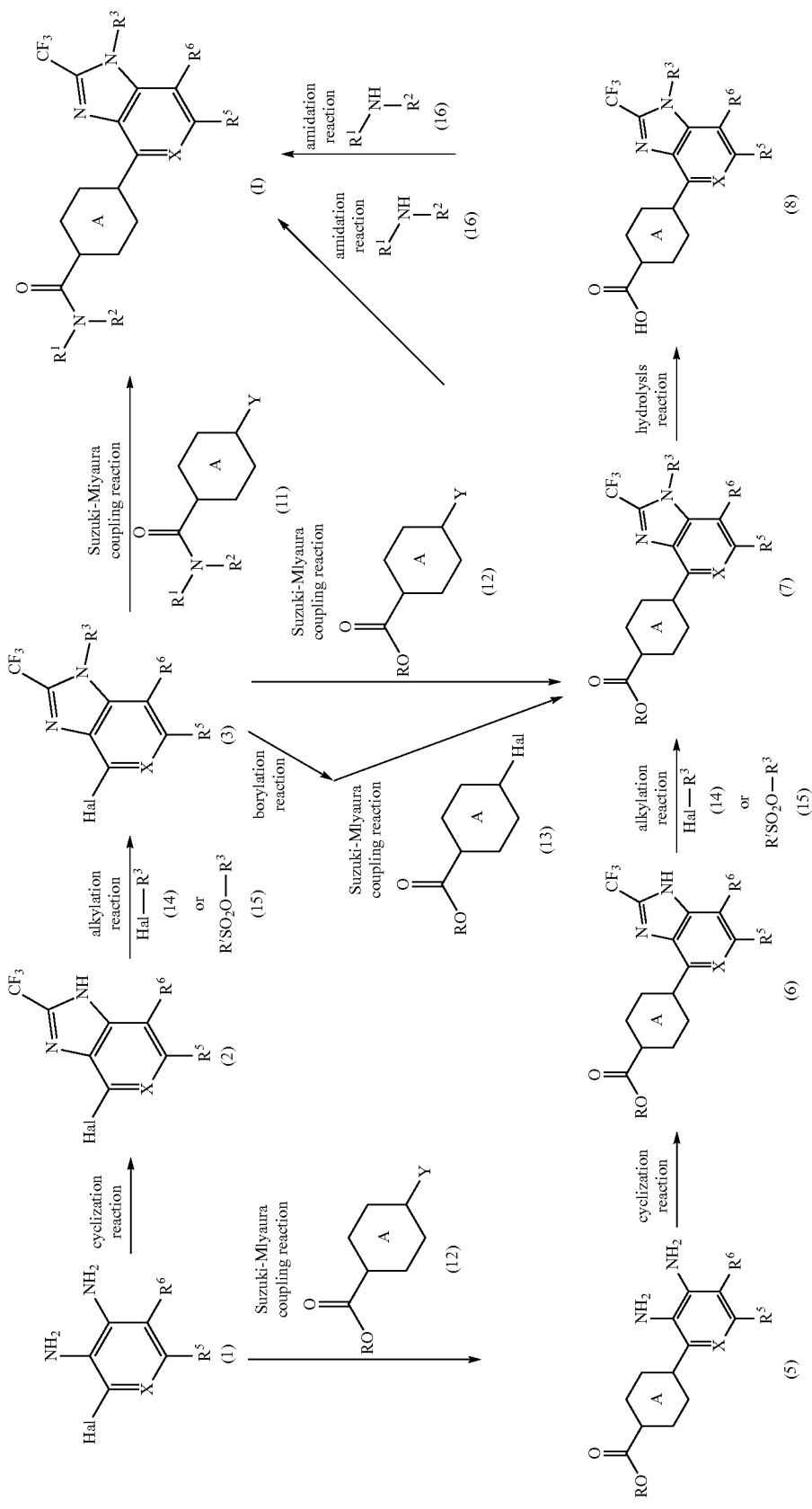

wherein Hal is a halogen atom, R is an optionally substituted $C_{1-6}$ alkyl group, R' is a methyl group, a trifluoromethyl group or a p-tolyl group, and Y is a boronic acid group (—B(OH)$_2$), a boronate ester group (—B(OR'')$_2$, a trifluoroborate group; R'' is a $C_{1-6}$ alkyl group) or a cyclic group thereof (e.g., 4,4,5,5-tetramethyl-1,3,2-dioxaborolan-2-yl, etc.), and the other symbols are as defined above.

Example of the "optionally substituted $C_{1-6}$ alkyl group" represented by R include those exemplified as the above-mentioned $R^3$ and the like.

Compound (I) can be produced by subjecting compound (3) to the Suzuki-Miyaura coupling reaction with compound (11).

Compound (I) can also be produced by subjecting compound (7) or compound (8) to an amidation reaction. Examples of the amidation reaction include a method of reacting compound (7) with compound (16) in the presence of an aluminium reagent such as bis(trimethylaluminium)-1,4-diazabicyclo[2.2.2]octane adduct and the like, and a method of condensing compound (8) with compound (16) using an activating agent such as HATU and the like.

Compound (3) can be produced by subjecting compound (2) to an alkylation reaction. The alkylation reaction can be carried out by reacting compound (2) with compound (14) or compound (15), in the presence of a base.

Compound (2) can be produced by subjecting compound (1) to a cyclization reaction with trifluoromethylacetic anhydride.

Compound (7) can be produced by subjecting compound (6) to an alkylation reaction. The alkylation reaction can be carried out by reacting compound (6) with compound (14) or compound (15), in the presence of a base.

Compound (7) can also be produced by subjecting compound (3) to the Suzuki-Miyaura coupling reaction with compound (12).

Compound (7) can also be produced by subjecting compound (3) to a borylation reaction, followed by the Suzuki-Miyaura coupling reaction with compound (13). The borylation reaction of compound (3) can be carried out by reacting compound (3) with a borylating reagent, in the presence of a palladium catalyst and a base. Examples of the borylating reagent include bispinacolatodiborane and the like.

Compound (8) can be produced by subjecting compound (7) to a hydrolysis reaction.

Compound (6) can be produced by subjecting compound (5) to a cyclization reaction with trifluoromethylacetic anhydride.

Compound (5) can be produced by subjecting compound (1) to the Suzuki-Miyaura coupling reaction with compound (12).

Compound (11) can be produced from compound (9) according to the following method.

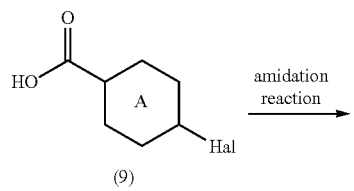

(9)

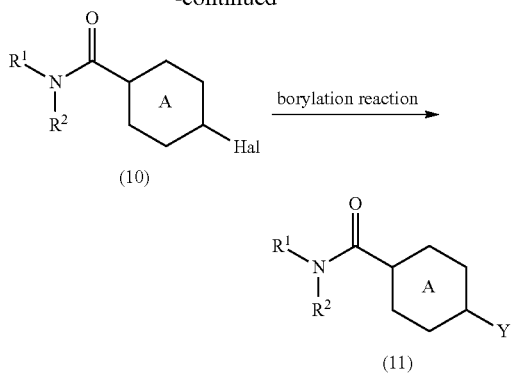

wherein each symbol is as defined above.

Compound (11) can be produced by subjecting compound (10) to a borylation reaction. The borylation reaction can be carried out by reacting compound (10) with a borylating reagent, in the presence of a palladium catalyst and a base. Examples of the borylating reagent include bispinacolatodiborane and the like.

Compound (10) can be produced by subjecting compound (9) to an amidation reaction.

Compound (12) can be produced from compound (13) according to the following method.

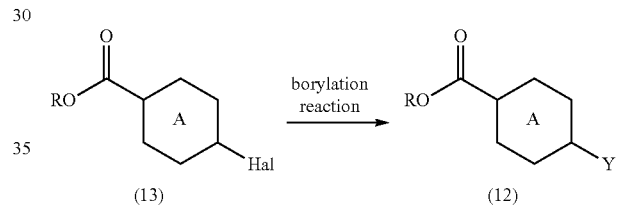

wherein each symbol is as defined above.

Compound (12) can be produced by subjecting compound (13) to a borylation reaction. The borylation reaction can be carried out by reacting compound (13) with a borylating reagent, in the presence of a palladium catalyst and a base. Examples of the borylating reagent include bispinacolatodiborane and the like.

Where necessary, in any of the above-mentioned reaction schemes, $R^1$-$R^6$, Hal, R and R' can also be converted by using a general organic reaction singly or using a plurality of general organic reactions in combination, for example, halogenation reaction, acylation reaction, sulfonylation reaction, alkylation reaction, hydrolysis reaction, amination reaction, amidation reaction, esterification reaction, etherification reaction, oxidation reaction, reduction reaction, protection reaction, deprotection reaction, coupling reaction, addition reaction, elimination reaction, substitution reaction and the like.

Compound (1), compound (9), compound (13), compound (14), compound (15) and compound (16) may be available commercially product, or can also be produced by a method known per se, or a method analogous thereto.

In the thus-obtained compound (I), an intramolecular functional group can also be converted to an object functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

In the above-mentioned production method, when a starting compound has an amino group, a carboxyl group, a hydroxy group, a carbonyl group or a mercapto group as a substituent, a protecting group generally used in the peptide chemistry may be introduced into these groups, and the object compound can be obtained by removing the protecting group as necessary after the reaction.

Compound (I) obtained by the above-mentioned production method can be isolated and purified by a known means, such as solvent extraction, liquid conversion, phase transfer, crystallization, recrystallization, chromatography and the like.

When compound (I) contains an optical isomer, a stereoisomer, a regioisomer and a rotamer, these compounds are also encompassed in compound (I), and each can be obtained as a single product according to a synthesis method or separation method known per se. For example, when an optical isomer exists in compound (I), the optical isomer resolved from the compound is also encompassed in compound (I).

The optical isomer can be produced according to a method known per se. Specifically, the optical isomer is obtained using an optically active synthetic intermediate or by subjecting the racemic final product to an optical resolution according to a known method.

The optical resolution may be a method known per se, such as a fractional recrystallization method, a chiral column method, a diastereomer method etc.

1) Fractional Recrystallized Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallized method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) as an eluent, solely or in admixture to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallized method, a chromatography method etc.) and the like, and is subjected to a chemical treatment such as hydrolysis and the like to separate an optically active reagent moiety, whereby an optical isomer is obtained. For example, when compound (I) contains a hydroxy group or a primary or secondary amino group in a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxy group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

Compound (I) may be a crystal. A single crystal form and a mixture of crystal forms are both encompassed in compound (I).

A crystal of compound (I) can be produced by crystallizing compound (I), by applying a crystallization method known per se.

In the present specification, the melting point means a melting point measured, for example, by micro melting point apparatus (Yanako, MP-500D or Buchi, B-545), DSC (differential scanning calorimetry analysis) apparatus (SEIKO, EXSTAR6000) and the like.

Generally, the melting point sometimes varies depending on the measurement device, measurement condition and the like. The crystal of compound (I) may be a crystal showing a melting point different from the values described in the present specification as long as the difference is within a general error range.

The crystal of compound (I) is superior in the physicochemical properties (e.g., melting point, solubility, stability) and biological properties (e.g., pharmacokinetics (absorbability, distribution, metabolism, excretion), efficacy expression), and is extremely useful as a medicament.

Furthermore, compound (I) may be a pharmaceutically acceptable cocrystal or cocrystal salt. The cocrystal or cocrystal salt means a crystalline substance constituted with two or more special solids at room temperature, each having different physical properties (e.g., structure, melting point, melting heat, hygroscopicity, solubility and stability). The cocrystal or cocrystal salt can be produced by a cocrystallization method known per se.

When compound (I) has an asymmetric center, isomers such as enantiomer, diastereomer and the like may be present. Such isomer and a mixture thereof are encompassed in the present invention. In addition, when isomer due to conformation or tautomerism is present, such isomer and a mixture thereof are also encompassed in compound (I) of the present invention.

Compound (I) may be used as a prodrug. A prodrug of compound (I) means a compound which is converted to compound (I) of the present invention with a reaction due to an enzyme, an gastric acid, etc. under the physiological condition in the living body, that is, a compound which is converted to compound (I) of the present invention with oxidation, reduction, hydrolysis, etc. according to an enzyme; a compound which is converted to compound (I) of the present invention by hydrolysis etc. due to gastric acid, etc.

A prodrug of compound (I) may be
a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.);
a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.);
a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.)
and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

In the present specification, a prodrug may form a salt, and examples of such salt include those exemplified as a salt of compound (I).

Compound (I) may be labeled with an isotope (e.g., $^3$H, $^{13}$C, $^{14}$C, $^{18}$F, $^{35}$S, $^{125}$I) and the like.

Compound (I) labeled with or substituted by an isotope can be used, for example, as a tracer used for Positron Emission Tomography (PET) (PET tracer), and expected to be useful in the field of medical diagnosis and the like.

Furthermore, compound (I) may be a hydrate or a non-hydrate, or a non-solvate (e.g., anhydride), or a solvate (e.g., hydrate).

Compound (I) also encompasses a deuterium conversion form wherein $^1$H is converted to $^2$H(D).

A medicament containing compound (I) (In the present specification, sometimes to be referred to as "the medicament of the present invention") can be used solely or as a pharmaceutical composition prepared by mixing with a pharmacologically acceptable carrier, according to a method known per se (e.g., the method described in the Japanese Pharmacopoeia etc.) as the production method of a pharmaceutical preparation.

As the "pharmacologically acceptable carrier", various organic or inorganic carrier substances conventionally used as preparation materials can be used. These are incorporated as excipient, lubricant, binder and disintegrant for solid preparations; or solvent, solubilizing agent, suspending agent, isotonicity agent, buffer and soothing agent for liquid preparations; and the like; and preparation additives such as preservative, antioxidant, colorant, sweetening agent and the like can be used as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil. Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the above-mentioned aqueous food tar color), natural dyes (e.g., p-carotene, chlorophyll, red iron oxide) and the like.

Preferable examples of the sweetening agent include saccharin sodium, dipotassium glycyrrhizinate, aspartame and stevia.

Examples of the dosage form of the medicament of the present invention include oral preparations such as tablet (including sugar-coated tablet, film-coated tablet, sublingual tablet, orally disintegrating tablet, buccal tablet), capsule (including soft capsule, microcapsule), pill, granule, powder, troche, syrup, liquid, emulsion, suspension, aerosol, films (e.g., orally disintegrable films, oral mucosa-adhesive film) and the like; and parenteral agents such as injection (e.g., subcutaneous injection, intravenous injection, intramuscular injection, intraperitoneal injection, drip infusion), external preparation (e.g., transdermal absorption type preparation, ointment, lotion, adhesive preparation), suppository (e.g., rectal suppository, vaginal suppository), pellet, nasal preparation, pulmonary preparation (inhalant), eye drop and the like. Compound (I) and the medicament of the present invention can be respectively safely administered orally or parenterally (e.g., intrarectal, intravenous, intraarterial, intramuscular, subcutaneous, intraorgan, intranasal, intradermal, instillation, intracerebral, intravaginal, intraperitoneal, intratumoral, proximal tumor administrations, and administration to the lesion).

These preparations may be a release control preparation (e.g., sustained-release microcapsule) such as an immediate-release preparation, a sustained-release preparation and the like.

While the content of compound (I) in the medicament of the present invention varies depending on the dosage form, dose of compound (I) and the like, it is, for example, about 0.1 to 100 wt %, preferably about 0.1 to 50 wt %, more preferably about 0.5 to 20 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar-coating base, sucrose is used, and one or more kinds selected from talc, and the precipitated calcium carbonate, gelatin, gum arabic, pullulan, carnauba wax and the like may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D-55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, red ferric oxide and the like may also be used during coating.

Compound (I) can be used as a prophylactic or therapeutic agent, or diagnostic agent for the below-mentioned various diseases in mammals (e.g., mice, rats, hamster, rabbits, cats, dogs, cows, sheep, monkeys, humans etc.). Compound (I) can be expected to be useful as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism spectrum disorder, adjustment disorder, bipolar disorder, neurosis, drug dependence, schizophrenia (e.g., positive symptom, negative symptom, cognitive impairment), neurosis, chronic fatigue syndrome, anxiety neurosis, compulsive neurosis, panic disorder, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression, cognitive impairment in major depression], (2) genetic diseases associated with psychiatric disorders and cognitive impairment [e.g., Rett syndrome, fragile X syndrome, Angelman's syndrome, tuberous sclerosis, RAS/MAPK syndromes (RASopathy) (e.g., neurofibromatosis type 1, Noonan syndrome, Noonan syndrome with multiple lentigines, Cardio-facio-cutaneous (CFC) syndrome, Costello syndrome, Legius syndrome, Leopard syndrome, capillary malformation-arteriovenous malformation (CM-AVM) syndrome, Parkes Weber syndrome, etc.), 22q11.2 deletion syndrome]

(3) neurodegenerative diseases [e.g., Alzheimer's disease, Alzheimer-type senile dementia, Parkinson's disease, Huntington's disease, dementia associated with Huntington's disease, multi-infarct dementia, frontotemporal dementia, Parkinson-type dementia, frontotemporal dementia Parkinson's Type, progressive supranuclear palsy, Pick's syndrome, Niemann-Pick syndrome, corticobasal degeneration, Down's disease, vascular dementia (VaD) (e.g., multi-infarct dementia, strategic single infarct dementia, Small vessel disease with dementia, hypoperfusion vascular dementia, hemorrhagic dementia, chronic subdural hematoma etc.), postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis, neurodegeneration accompanying stroke, neurodegeneration accompanying cerebral infarction], (4) age-related cognition memory disorders [e.g., age-related memory disorders, senile dementia]

(5) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (6) respiratory depression caused by anesthetics, traumatic disease, or neurodegenerative disease and the like, (7) traumatic brain injury, stroke, cerebral infarction, cerebral apoplexy, hearing loss, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, autoimmune encephalitis (e.g., autoimmune limbic encephalitis), immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, stress ulcer, diarrhea, constipation, postoperative ileus, stress gastrointestinal disorder, and the like.

In particular, compound (I) can be expected to be useful as an agent for the prophylaxis or treatment of depression, Alzheimer's disease, schizophrenia, attention deficit hyperactivity disorder (ADHD) and the like.

Since compound (I) has an excellent AMPA receptor potentiator effect, it is expected to provide an excellent prophylactic or therapeutic effect for the above-mentioned diseases.

Compound (I) shows excellent solubility in water, the second solution of Japanese Pharmacopeia Elution Test, or the second solution of Japanese Pharmacopoeia Disintegration Test, shows excellent in vivo kinetics (e.g., plasma drug half-life, intracerebral migration, metabolic stability, CYP inhibition), shows low toxicity (e.g., more excellent as a medicament in terms of acute toxicity, chronic toxicity, genetic toxicity, reproductive toxicity, cardiotoxicity, drug interaction, carcinogenicity, phototoxicity, and the like), and also has excellent properties as a pharmaceutical product such as a few side effects. Therefore, compound (I) can be safely administered orally or parenterally to a mammal (e.g., mouse, rat, hamster, rabbit, cat, dog, bovine, sheep, monkey, human and the like).

The dose of compound (I) varies depending on the subject of administration, administration route and symptoms and is not particularly limited. For example, for oral administration to adult patients (body weight adult 40 to 80 kg, for example, 60 kg) with the above-mentioned disease, the dose may be, for example, 0.001 to 1000 mg/kg body weight/day, preferably 0.01 to 100 mg/kg body weight/day, more preferably 0.1 to 10 mg/kg body weight/day, as compound (I). This amount can be administered in one to three portions per day.

It is also possible to apply compound (I) to each of the above-mentioned diseases in combination with a drug, or as a combination therapy in combination with therapy method, generally used for the disease.

Examples of other active ingredients (hereinafter, to be referred to as concomitant drug) to be used in combination with compound (I) include the following drugs.
benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-$HT_{1A}$ agonist (buspirone hydrochloride, tandospirone citrate, osemozotan hydrocloride etc.), 5-$HT_3$ antagonist (Cyamemazine etc.), heart non-selective β inhibitor (propranolol hydrochloride, oxprenolol hydrochloride, pindolol etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other anti-anxiety drug (meprobamate etc.), tachykinin antagonist (aprepitant, saredutant etc.), medicament that acts on metabotropic glutamate receptor, medicament that acts on GABA receptor, medicament that acts on acetylcholine receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (ketamine, S-ketamine, R-ketamine, ketamine metabolite (e.g., (2S,6S; 2R,6R)-hydroxynnorketamine, (2R,6R)-hydroxynnorketamine etc.), memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium (e.g., lithium carbonate etc.), sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for ALS (riluzole etc., neurotrophic factor etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin, indomethacin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining compound (I) and a concomitant drug, a superior effect such as
(1) the dose can be reduced as compared to single administration of compound (I) or a concomitant drug, (2) the drug to be combined with compound (I) can be selected according to the condition of patients (mild case, severe case and the like),
(3) the period of treatment can be set longer by selecting a concomitant drug having different action and mechanism from compound (I),
(4) a sustained treatment effect can be designed by selecting a concomitant drug having different action and mechanism from compound (I),
(5) a synergistic effect can be afforded by a combined use of compound (I) and a concomitant drug, and the like, can be achieved.

Hereinafter the compound of the present invention and a concomitant drug used in combination are referred to as the "combination agent of the present invention".

When using the combination agent of the present invention, the administration time of compound (I) and the concomitant drug is not restricted, and compound (I) or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that compound (I) and the concomitant drug are combined in administration. Examples of such administration mode include the following methods:
(1) administration of a single preparation obtained by simultaneously processing compound (I) and the concomitant drug, (2) simultaneous administration of two kinds of preparations of compound (I) and the concomitant drug, which have been separately produced, by the same administration route, (3) administration of two kinds of preparations of compound (I) and the concomitant drug, which have been separately produced, by the same administration route in a staggered manner, (4) simultaneous administration of two kinds of preparations of compound (I) and the concomitant drug, which have been separately produced, by different administration routes, (5) administration of two kinds of preparations of compound (I) and the concomitant drug, which have been separately produced, by different administration routes in a staggered manner (for example, administration in the order of the compound of the present invention and the concomitant drug, or in the reverse order) and the like.

The combination agent of the present invention can be used as a pharmaceutical composition prepared by mixing compound (I) or(and) the above-mentioned concomitant drug with a pharmacologically acceptable carrier, like the medicament of the present invention.

The dosage of the concomitant drug may be appropriately selected according to the dose clinically used. The mixing ratio of compound (I) to the concomitant drug can be appropriately selected depending on administration subject, route of administration, target disease, symptom, combination and the like.

For example, the content of compound (I) in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation. When compound (I) and a concomitant drug are separately formulated into preparations, the contents thereof are similar to the above.

EXAMPLES

The present invention is explained in detail in the following by referring to Examples, Experimental Examples and Formulation Examples. However, the examples do not limit the present invention and the examples can be modified within the scope of the present invention.

The "room temperature" in the following Examples is generally about 10° C. to about 35° C. The ratio for mixed solvent is, unless otherwise specified, a volume mixing ratio and % means wt % unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as an eluent, and UV detector was used for the detection. In silica gel column chromatography, the indication of NH means use of aminopropylsilane-bonded silica gel and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

The unit of sample concentration (c) for optical rotation ($[\alpha]_D$) is g/100 mL.

Elemental analysis value (Anal.) is described as calculated value (Calcd) and actual measured value (Found).

In the following Examples, the following abbreviations are used.
mp: melting point
MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
TFA: trifluoroacetic acid
DMA: N,N-dimethylacetamide
DMF: N,N-dimethylformamide
THF: tetrahydrofuran
DME: 1,2-dimethoxyethane
MeOH: methanol
TEA: triethylamine HATU: O-(7-azabenzotriazol-1-yl)-N,N,N',N'-tetramethyluronium hexafluorophosphate
DIPEA: N-ethyl-N-isopropylpropan-2-amine Example 10

(4-(1-(2,2-difluoroethyl)-2-(trifluoromethyl)-1H-imidazo[4,5-c]pyridin-4-yl)-2-fluorophenyl)(morpholin-4-yl)methanone A) methyl 4-(3,4-diaminopyridin-2-yl)-2-fluorobenzoate A mixture of 2-chloropyridine-3,4-diamine (1.00 g), 3-fluoro-4-(methoxycarbonyl)phenylboronic acid (1.66 g), [1,1'-bis(diphenylphosphino)ferrocene]palladium(II) dichloride dichloromethane adduct (0.57 g), potassium carbonate (1.92 g), DME (15 mL) and water (4 mL) was irradiated with microwave at 130° C. for 30 min. To the reaction mixture was added water at room temperature, and the mixture was extracted with ethyl acetate. The organic layer was separated, dried over anhydrous magnesium sulfate, and concentrated under reduced pressure. The residue was purified by silica gel column chromatography (NH, ethyl acetate/hexane) to give the title compound (1.23 g).
MS: [M+H]$^+$ 262.0.

B) methyl 2-fluoro-4-(2-(trifluoromethyl)-1H-imidazo[4,5-c]pyridin-4-yl)benzoate A mixture of methyl 4-(3,4-diaminopyridin-2-yl)-2-fluorobenzoate (1.23 g), TFA (7 mL) and toluene (7 mL) was irradiated with microwave at 120° C. for 1 hr, and then irradiated with microwave at 140° C. for 2 hr. The reaction mixture was concentrated, saturated aqueous sodium hydrogencarbonate solution was added thereto, and the mixture was extracted with ethyl acetate. The organic layer was separated, dried over anhydrous magnesium sulfate, and concentrated under reduced pressure. The residue was purified by silica gel column chromatography (ethyl acetate/hexane) to give the title compound (1.00 g).
MS: [M+H]$^+$ 339.9.

C) methyl 4-(1-(2,2-difluoroethyl)-2-(trifluoromethyl)-1H-imidazo[4,5-c]pyridin-4-yl)-2-fluorobenzoate To a mixture of methyl 2-fluoro-4-(2-(trifluoromethyl)-1H-imidazo[4,5-c]pyridin-4-yl)benzoate (500 mg), potassium carbonate (407 mg) and DMF (5 mL) was added 2,2-difluoroethyl trifluoromethanesulfonate (379 mg) at room temperature. The reaction mixture was stirred at room temperature for 2 hr, and 2,2-difluoroethyl trifluoromethanesulfonate (189 mg) was added thereto. The reaction mixture was stirred at room temperature for 2 hr, water was added thereto, and the mixture was extracted with ethyl acetate. The organic layer was separated, dried over anhydrous magnesium sulfate, and concentrated under reduced pressure. The residue was purified by silica gel column chromatography (ethyl acetate/hexane) to give the title compound (477 mg).
MS: [M+H]$^+$ 404.0.

D) 4-(1-(2,2-difluoroethyl)-2-(trifluoromethyl)-1H-imidazo[4,5-c]pyridin-4-yl)-2-fluorobenzoic acid To a mixture of methyl 4-(1-(2,2-difluoroethyl)-2-(trifluoromethyl)-1H-imidazo[4,5-c]pyridin-4-yl)-2-fluorobenzoate (440 mg), MeOH (5 mL) and THF (7 mL) was added 1N aqueous sodium hydroxide solution (5 mL) at 0° C. The reaction mixture was stirred at room temperature for 2 hr, 1N hydrochloric acid was added thereto, and the mixture was extracted with a mixed solvent of ethyl acetate and THF. The organic layer was separated, dried over anhydrous magnesium sulfate, and concentrated under reduced pressure. The residue was purified by silica gel column chromatography (ethyl acetate/hexane) to give the title compound (176 mg).
MS: [M+H]$^+$ 389.9.

E) (4-(1-(2,2-difluoroethyl)-2-(trifluoromethyl)-1H-imidazo[4,5-c]pyridin-4-yl)-2-fluorophenyl)(morpholin-4-yl)methanone To a mixture of 4-(1-(2,2-difluoroethyl)-2-(trifluoromethyl)-1H-imidazo[4,5-c]pyridin-4-yl)-2-fluorobenzoic acid (50.0 mg), HATU (73.3 mg), DIPEA (49.8 mg) and DMF (1 mL) was added morpholine (23.0 μl) at room temperature. The reaction mixture was stirred at room temperature for 12 hr, water was added thereto, and the mixture was extracted with ethyl acetate. The organic layer was separated, dried over anhydrous magnesium sulfate, and concentrated under reduced pressure. The residue was purified by silica gel column chromatography (ethyl acetate/hexane), and recrystallized from ethyl acetate/hexane to give the title compound (26.0 mg).
$^1$H NMR (300 MHz, DMSO-d$_6$) δ 3.32-3.37 (2H, m), 3.57 (2H, t, J=4.5 Hz), 3.68 (4H, s), 5.09 (2H, t, J=15.1 Hz), 6.36-6.79 (1H, m), 7.64 (1H, t, J=7.7 Hz), 7.96 (1H, d, J=5.7 Hz), 8.49 (1H, dd, J=11.3, 1.5 Hz), 8.59 (1H, dd, J=7.9, 1.5 Hz), 8.72 (1H, d, J=5.7 Hz).

Example 15

(4-(1-(2,2-difluoroethyl)-2-(trifluoromethyl)-1H-imidazo[4,5-c]pyridin-4-yl)-2-fluorophenyl)(1,4-oxazepan-4-yl)methanone A) methyl 4-(3,4-diaminopyridin-2-yl)-2-fluorobenzoate A mixture of 2-chloropyridine-3,4-diamine (1.00 g), 3-fluoro-4-(methoxycarbonyl)phenylboronic acid (1.66 g), [1,1'-bis(diphenylphosphino)ferrocene]palladium(II) dichloride dichloromethane adduct (0.57 g), potassium carbonate (1.92 g), DME (15 mL) and water (4 mL) was irradiated with microwave at 130° C. for 30 min. To the reaction mixture was added water at room temperature, and the mixture was extracted with ethyl acetate. The organic layer was separated, dried over anhydrous magnesium sulfate, and concentrated under reduced pressure. The residue was purified by silica gel column chromatography (NH, ethyl acetate/hexane) to give the title compound (1.23 g).
MS: [M+H]$^+$ 262.0.

B) methyl 2-fluoro-4-(2-(trifluoromethyl)-1H-imidazo[4,5-c]pyridin-4-yl)benzoate A mixture of methyl 4-(3,4-diaminopyridin-2-yl)-2-fluorobenzoate (1.23 g), TFA (7 mL) and toluene (7 mL) was irradiated with microwave at 120° C. for 1 hr, and then irradiated with microwave at 140° C. for 2 hr. The reaction mixture was concentrated, saturated aqueous sodium hydrogencarbonate solution was added thereto, and the mixture was extracted with ethyl acetate. The organic layer was separated, dried over anhydrous magnesium sulfate, and concentrated under reduced pressure. The residue was purified by silica gel column chromatography (ethyl acetate/hexane) to give the title compound (1.00 g).

MS: [M+H]$^+$ 339.9.

C) methyl 4-(1-(2,2-difluoroethyl)-2-(trifluoromethyl)-1H-imidazo[4,5-c]pyridin-4-yl)-2-fluorobenzoate To a mixture of methyl 2-fluoro-4-(2-(trifluoromethyl)-1H-imidazo[4,5-c]pyridin-4-yl)benzoate (500 mg), potassium carbonate (407 mg) and DMF (5 mL) was added 2,2-difluoroethyl trifluoromethanesulfonate (379 mg) at room temperature. The reaction mixture was stirred at room temperature for 2 hr, and 2,2-difluoroethyl trifluoromethanesulfonate (189 mg) was added thereto. The reaction mixture was stirred at room temperature for 2 hr, water was added thereto, and the mixture was extracted with ethyl acetate. The organic layer was separated, dried over anhydrous magnesium sulfate, and concentrated under reduced pressure. The residue was purified by silica gel column chromatography (ethyl acetate/hexane) to give the title compound (477 mg).

MS: [M+H]$^+$ 404.0.

D) (4-(1-(2,2-difluoroethyl)-2-(trifluoromethyl)-1H-imidazo[4,5-c]pyridin-4-yl)-2-fluorophenyl)(1,4-oxazepan-4-yl)methanone A mixture of methyl 4-(1-(2,2-difluoroethyl)-2-(trifluoromethyl)-1H-imidazo[4,5-c]pyridin-4-yl)-2-fluorobenzoate (280 mg), bis(trimethylaluminium)-1,4-diazabicyclo[2.2.2]octane adduct (534 mg), 1,4-oxazepane hydrochloride (287 mg) and THF (3 mL) was irradiated with microwave at 110° C. for 1 hr. To the reaction mixture was added water at room temperature, and the mixture was extracted with ethyl acetate. The organic layer was separated, dried over anhydrous magnesium sulfate, and concentrated under reduced pressure. The residue was purified by silica gel column chromatography (ethyl acetate/hexane), and recrystallized from ethyl acetate/hexane to give the title compound (112 mg).

$^1$H NMR (300 MHz, CDCl$_3$) δ 1.81-1.95 (1H, m), 2.09 (1H, dt, J=12.2, 6.2 Hz), 3.42-4.01 (8H, m), 4.72 (2H, td, J=13.2, 3.8 Hz), 5.83-6.38 (1H, m), 7.43-7.61 (2H, m), 8.43-8.54 (1H, m), 8.59 (1H, dt, J=8.2, 1.9 Hz), 8.70 (1H, d, J=5.7 Hz).

Example 35

(5-(1-(2,2-difluoroethyl)-2-(trifluoromethyl)-1H-benzimidazol-4-yl)-3-fluoropyridin-2-yl)(morpholin-4-yl)methanone

A) (5-bromo-3-fluoropyridin-2-yl)(morpholin-4-yl)methanone

To a mixture of 5-bromo-3-fluoropyridine-2-carboxylic acid (3.00 g), THF (30 mL) and DMF (two drops by pasteur pipette) was added oxalyl dichloride (3.57 mL) at 0° C. The reaction mixture was stirred at room temperature for 2 hr, and concentrated under reduced pressure. To the residue was added THF (30 mL), and TEA (2.85 mL) and morpholine (1.78 mL) were added thereto at 0° C. The reaction mixture was stirred at room temperature for 12 hr, water was added thereto, and the mixture was extracted with ethyl acetate. The organic layer was separated, dried over anhydrous magnesium sulfate, and concentrated under reduced pressure. The residue was purified by silica gel column chromatography (NH, ethyl acetate/hexane) to give the title compound (3.10 g).

MS: [M+H]$^+$ 288.9

B) (3-fluoro-5-(4,4,5,5-tetramethyl-1,3,2-dioxaborolan-2-yl)pyridin-2-yl)(morpholin-4-yl)methanone A mixture of (5-bromo-3-fluoropyridin-2-yl)(morpholin-4-yl)methanone (3.10 g), 4,4,4',4',5,5,5',5'-octamethyl-2,2'-bi-1,3,2-dioxaborolane (3.27 g), potassium acetate (2.11 g), [1,1'-bis(diphenylphosphino)ferrocene]palladium(II) dichloride dichloromethane adduct (0.438 g) and DME (73.4 mL) was stirred under nitrogen atmosphere at 80° C. for 4 hr. To the reaction mixture was added water at room temperature, and the mixture was extracted with ethyl acetate. The organic layer was separated, washed with water and saturated brine, dried over anhydrous magnesium sulfate, and concentrated under reduced pressure. The obtained residue was used as a crude product in the next reaction.

MS: [M+H]$^+$ 337.2

C) 4-bromo-1-(2,2-difluoroethyl)-2-(trifluoromethyl)-1H-benzimidazole

A mixture of 3-bromobenzene-1,2-diamine (1.35 g), TFA (12 mL) and toluene (6 mL) was irradiated with microwave at 110° C. for 30 min. The reaction mixture was concentrated, saturated aqueous sodium hydrogencarbonate solution was added thereto, and the mixture was extracted with ethyl acetate. The organic layer was separated, dried over anhydrous magnesium sulfate, and concentrated under reduced pressure. To the residue were added DMA (20 mL), potassium carbonate (2.99 g) and 2,2-difluoroethyl trifluoromethanesulfonate (1.85 g) at room temperature. The reaction mixture was stirred at room temperature for 12 hr, water was added thereto, and the mixture was extracted with ethyl acetate. The organic layer was separated, dried over anhydrous magnesium sulfate, and concentrated under reduced pressure. The residue was purified by silica gel column chromatography (ethyl acetate/hexane) to give the title compound (2.00 g).

MS: [M+H]$^+$ 328.8.

D) (5-(1-(2,2-difluoroethyl)-2-(trifluoromethyl)-1H-benzimidazol-4-yl)-3-fluoropyridin-2-yl)(morpholin-4-yl)methanone To a mixture of 4-bromo-1-(2,2-difluoroethyl)-2-(trifluoromethyl)-1H-benzimidazole (1.96 g) and toluene (40.8 mL) were added (3-fluoro-5-(4,4,5,5-tetramethyl-1,3,2-dioxaborolan-2-yl)pyridin-2-yl)(morpholin-4-yl)methanone obtained in the above-mentioned Step B), bis(di-tert-butyl (4-dimethylaminophenyl)phosphine)dichloropalladium(II) (0.401 g) and 2M aqueous sodium carbonate solution (5.96 mL) at room temperature. The mixture was stirred under nitrogen atmosphere at 100° C. for 8 hr. To the reaction mixture was added water, and the mixture was extracted with ethyl acetate. The organic layer was dried over anhydrous magnesium sulfate, and concentrated under reduced pressure. The residue was purified by silica gel column chromatography (ethyl acetate/hexane). The residue was washed with diisopropyl ether to give the title compound (2.30 g) as a crude product. The crude product (2.30 g) was recrystallized from ethyl acetate/hexane to give the title compound (2.17 g).

$^1$H NMR (300 MHz, DMSO-d$_6$) δ 3.36 (2H, t, J=4.6 Hz), 3.51-3.63 (2H, m), 3.71 (4H, s), 4.96-5.22 (2H, m), 6.33-6.80 (1H, m), 7.62-7.75 (1H, m), 7.87 (1H, d, J=7.2 Hz), 7.98 (1H, d, J=8.1 Hz), 8.52 (1H, dd, J=11.0, 1.5 Hz), 9.17 (1H, s).

Example 35-2

(5-(1-(2,2-difluoroethyl)-2-(trifluoromethyl)-1H-benzimidazol-4-yl)-3-fluoropyridin-2-yl)(morpholin-4-yl)methanone A) 5-bromo-3-fluoropicoline acid 5-Bromo-3-fluoropicolinonitrile (25 g) and conc. hydrochloric acid (125 mL) were stirred at 70° C. for 39 hr. The mixture was cooled to 0° C., 8 M aqueous sodium hydroxide solution (187 mL) was added thereto, and the mixture was stirred for 1 hr. The solid was collected, washed with cooled water (50 mL), dried overnight in air, and then dried under reduced pressure at 60° C. for 5 hr to give the title compound (22.6 g).

MS: [M+H]$^+$ 219.7.

B) (5-bromo-3-fluoropyridin-2-yl)(morpholin-4-yl)methanone

To a mixture of 5-bromo-3-fluoropicoline acid (22.6 g), DMF (0.397 mL) and THF (270 mL) was added thionyl chloride (11.2 mL) at room temperature, and the mixture was stirred overnight. The mixture was concentrated under reduced pressure (toluene was added thereto, and concentrated twice under reduced pressure). To the residue was added THF (230 mL), and triethylamine (42.9 mL) was added thereto while keeping the internal temperature 10° C. or below. Morpholine (9.73 mL) was added thereto at 0° C., and the mixture was stirred at the same temperature for 1.5 hr. To the reaction solution was added water (80 mL) at 0° C., and the mixture was extracted with ethyl acetate (500 mL). The organic layer was separated, washed with water (80 mL), 13% brine (80 mL×2) and saturated brine (40 mL), dried over magnesium sulfate, and concentrated under reduced pressure to give the title compound (26.1 g) as a crude product.

MS: [M+H]$^+$ 288.8.

C) (3-fluoro-5-(4,4,5,5-tetramethyl-1,3,2-dioxaborolan-2-yl)pyridin-2-yl)(morpholin-4-yl)methanone To a solution of the crude product (25.4 g) of (5-bromo-3-fluoropyridin-2-yl)(morpholin-4-yl)methanone, bis(pinacolato)diboron (26.8 g) and potassium acetate (17.3 g) in DME (440 mL) was added (1,1'-bis(diphenylphosphino)ferrocene)palladium(II) dichloride (1.93 g) under nitrogen atmosphere at 80° C., and the mixture was stirred for 2 hr. The mixture was cooled to room temperature, and water (100 mL) and ethyl acetate (100 mL) were added thereto. The mixture was stirred for 30 min, and filtered through Celite. The Celite was washed with ethyl acetate (50 mL). The filtrate was diluted with ethyl acetate (500 mL), and the organic layer was separated. The obtained organic layer was washed with water (250 mL and 150 mL) and saturated brine (125 mL), dried over magnesium sulfate, and concentrated under reduced pressure to give the title compound (44.2 g) as a crude product.

MS$^+$: 254.9. (detected as boronic acid)

D) (3-fluoro-5-(3-fluoro-2-nitrophenyl)pyridin-2-yl)(morpholin-4-yl)methanone

To a solution of the crude product (29.6 g) of (3-fluoro-5-(4,4,5,5-tetramethyl-1,3,2-dioxaborolan-2-yl)pyridin-2-yl)(morpholin-4-yl)methanone, 2-bromo-6-fluoronitrobenzene (17.6 g), 2-dicyclohexylphosphino-2',6'-dimethoxy-1,1'-biphenyl (1.31 g) and 2M aqueous sodium carbonate solution (120 mL) in toluene (400 mL) was added tris(dibenzylideneacetone)dipalladium(0) (1.46 g) under nitrogen atmosphere at room temperature, and the mixture was stirred at 80° C. for 16 hr. The mixture was cooled to room temperature, and water (180 mL) and ethyl acetate (120 mL) were added thereto. The mixture was stirred at room temperature for min, and filtered through Celite. The Celite was washed with ethyl acetate (about 300 mL). The organic layer was separated, washed with water (120 mL×2), and concentrated under reduced pressure. The residue was diluted with ethyl acetate (558 mL), NH silica gel (93 g) was added thereto, and the mixture was stirred for 14 hr. The mixture was filtered, and the silica gel was washed with a mixed solvent of ethyl acetate-hexane (1:1, 1000 mL), and the filtrate was concentrated under reduced pressure to give the title compound (31.0 g).

MS: [M+H]$^+$ 350.0.

E) (5-(3-((2,2-difluoroethyl)amino)-2-nitrophenyl)-3-fluoropyridin-2-yl)(morpholin-4-yl)methanone A mixture of (3-fluoro-5-(3-fluoro-2-nitrophenyl)pyridin-2-yl)(morpholin-4-yl)methanone (27.9 g), 2,2-difluoroethanamine (11.2 mL), diisopropylethylamine (55.9 mL) and DMSO (280 mL) was stirred under nitrogen atmosphere at 70° C. for 24 hr. The mixture was cooled to room temperature, water (111 mL) was added thereto at the temperature lower than 30° C. (the precipitate was generated), and then water (167 mL) was added thereto, and the mixture was stirred for 30 min. Next, water (279 mL) was added thereto, and the mixture was stirred for additional 30 min. The precipitated solid was collected, washed with water, dried overnight in air, and then dried at 50° C. for 3 hr under reduced pressure to give the title compound (28.5 g) as a crude product. This was dissolved in ethyl acetate (400 mL) at 65° C., heptane (200 mL) was added thereto, and the mixture was stirred for 15 min. The mixture was cooled to room temperature (<30° C.), and the mixture was stirred for 1 hr. The obtained crystals were collected, washed with heptane/ethyl acetate (4:1, 300 mL), and dried under reduced pressure at 50° C. for 1 hr to give the title compound (19.9 g).

MS: [M+H]$^+$ 411.1.

F) (5-(2-amino-3-((2,2-difluoroethyl)amino)phenyl)-3-fluoropyridin-2-yl)(morpholin-4-yl)methanone A mixture of (5-(3-((2,2-difluoroethyl)amino)-2-nitrophenyl)-3-fluoropyridin-2-yl)(morpholin-4-yl)methanone (20.7 g), 10% palladium-carbon (2.0 g) and THF (375 mL) was subjected to hydrogenation under balloon pressure at room temperature for 4 hr. The catalyst was removed by filtration, and the filtrate was concentrated under reduced pressure. Toluene was added thereto, and the mixture was again concentrated under reduced pressure to give the title compound.

MS: [M+H]$^+$ 381.2.

G) (5-(1-(2,2-difluoroethyl)-2-(trifluoromethyl)-1H-benzimidazol-4-yl)-3-fluoropyridin-2-yl)(morpholin-4-yl)methanone Trifluoroacetic anhydride (70.5 mL) was added to a solution of (5-(2-amino-3-((2,2-difluoroethyl)amino)phenyl)-3-fluoropyridin-2-yl)(morpholin-4-yl)methanone (76 g) in THF (1500 mL) at 0° C. The mixture was stirred for 0.5 hr, and concentrated under reduced pressure. To the residue was added acetic acid (760 mL), and the mixture was stirred overnight at 70° C. The mixture was concentrated under reduced pressure, to the residue were added ethyl acetate (795 mL) and heptane (516 mL) at 60° C., and the mixture was stirred for 15 min. Heptane (675 mL) was added thereto again, and the mixture was slowly cooled to room temperature, and stirred overnight. The precipitated crystals were collected, washed with a mixed solvent of ethyl acetate-heptane (1:5, 60 mL), and dried under reduced pressure at 50° C. for 1 hr to give the title compound (71 g). The title compound (96 g) was dissolved in ethyl acetate (840 mL) at 60° C., and filtered through filter paper, and the filter paper was washed with ethyl acetate (10 mL). Heptane (425 mL) was added thereto at 55-65° C., and the mixture was stirred for 30 min. Heptane (850 mL) was again added thereto, and the mixture was stirred for 30 min. The mixture was slowly cooled to 30° C., and the mixture was stirred for 1 hr. The precipitated crystals were collected, washed with a mixed solvent of ethyl acetate-heptane (1:4, 250 mL), and dried under reduced pressure at 50° C. for 30 min to give the title compound (90 g). These crystals were passed through a 16-mesh sieve, and pulverized with a jet mill to give the title compound (82 g).

$^1$H NMR (300 MHz, DMSO-d$_6$) δ 3.33-3.41 (2H, m), 3.54-3.63 (2H, m), 3.71 (4H, s), 4.98-5.17 (2H, m), 6.35-6.79 (1H, m), 7.64-7.74 (1H, m), 7.87 (1H, dd, J=7.6, 0.8 Hz), 7.98 (1H, d, J=7.9 Hz), 8.53 (1H, dd, J=10.8, 1.7 Hz), 9.17 (1H, t, J=1.7 Hz).

Example 46

(6-(1-(2,2-difluoroethyl)-2-(trifluoromethyl)-1H-benzimidazol-4-yl)pyridin-3-yl)(6,6-difluoro-1,4-oxazepan-4-yl)methanone A) 4-bromo-1-(2,2-difluoroethyl)-2-(trifluoromethyl)-1H-benzimidazole A mixture of 3-bromobenzene-1,2-diamine (1.35 g), TFA (12 mL) and toluene (6 mL) was irradiated with microwave at 110° C. for 30 min. The reaction mixture was concentrated, saturated aqueous sodium hydrogencarbonate solution was added thereto, and the mixture was extracted with ethyl acetate. The organic layer was separated, dried over anhydrous magnesium sulfate, and concentrated under reduced pressure. To the residue were added DMA (20 mL), potassium carbonate (2.99 g) and 2,2-difluoroethyl trifluoromethanesulfonate (1.85 g) at room temperature. The reaction mixture was stirred at room temperature for 12 hr, water was added thereto, and the mixture was extracted with ethyl acetate. The organic layer was separated, dried over anhydrous magnesium sulfate, and concentrated under reduced pressure. The residue was purified by silica gel column chromatography (ethyl acetate/hexane) to give the title compound (2.00 g).

MS: [M+H]$^+$ 328.8.

B) 1-(2,2-difluoroethyl)-4-(4,4,5,5-tetramethyl-1,3,2-dioxaborolan-2-yl)-2-(trifluoromethyl)-1H-benzimidazole A mixture of 4-bromo-1-(2,2-difluoroethyl)-2-(trifluoromethyl)-1H-benzimidazole (300 mg), 4,4,4',4',5,5,5',5'-octamethyl-2,2'-bi-1,3,2-dioxaborolane (278 mg), [1,1'-bis(diphenylphosphino)ferrocene]palladium(II) dichloride dichloromethane adduct (33.4 mg), potassium acetate (179 mg) and DME (5 mL) was stirred under nitrogen atmosphere at 80° C. for 4 hr. To the reaction mixture was added water, and the mixture was extracted with ethyl acetate. The organic layer was separated, dried over anhydrous magnesium sulfate, and concentrated under reduced pressure. The residue was used as a crude product of the title compound in the next reaction.

C) methyl 6-(1-(2,2-difluoroethyl)-2-(trifluoromethyl)-1H-benzimidazol-4-yl)

A mixture of 1-(2,2-difluoroethyl)-4-(4,4,5,5-tetramethyl-1,3,2-dioxaborolan-2-yl)-2-(trifluoromethyl)-1H-benzimidazole obtained in the above-mentioned Step B), methyl 6-chloronicotinate (234 mg), bis(di-tert-butyl(4-dimethylaminophenyl)phosphine)dichloropalladium(II) (61.2 mg), 2M aqueous sodium carbonate solution (0.91 mL) and toluene (2 mL) was stirred under nitrogen atmosphere at 100° C. for 16 hr. To the reaction mixture was added water, and the mixture was extracted with ethyl acetate. The organic layer was separated, dried over anhydrous sodium sulfate, and concentrated under reduced pressure. The residue was purified by silica gel column chromatography (ethyl acetate/hexane), and the obtained solid was washed with diisopropyl ether to give the title compound (208 mg).

MS: [M+H]$^+$ 386.0.

D) (6-(1-(2,2-difluoroethyl)-2-(trifluoromethyl)-1H-benzimidazol-4-yl)pyridin-3-yl)(6,6-difluoro-1,4-oxazepan-4-yl)methanone A mixture of methyl 6-(1-(2,2-difluoroethyl)-2-(trifluoromethyl)-1H-benzimidazol-4-yl)nicotinate (100 mg), bis(trimethylaluminium)-1,4-diazabicyclo[2.2.2]octane adduct (133 mg), 6,6-difluoro-1,4-oxazepane hydrochloride (90.0 mg) and THF (1.5 mL) was irradiated with microwave at 110° C. for 1 hr. To the mixture was added water, and the mixture was extracted with ethyl acetate. The organic layer was separated, dried over anhydrous magnesium sulfate, and concentrated under reduced pressure. The residue was purified by silica gel column chromatography (ethyl acetate/hexane), and recrystallized from ethyl acetate/hexane to give the title compound (50.9 mg).

$^1$H NMR (300 MHz, CDCl$_3$) δ 3.56-4.39 (8H, m), 4.74 (2H, td, J=13.1, 4.2 Hz), 5.75-6.40 (1H, m), 7.47-7.73 (2H, m), 7.92 (1H, dd, J=8.2, 2.4 Hz), 8.39 (1H, dd, J=6.8, 1.7 Hz), 8.81 (1H, dd, J=2.3, 0.8 Hz), 8.96 (1H, d, J=8.3 Hz).

The compounds of Examples are shown in the following Table 1-1 to Table 1-9. MS in the tables means actual measured value. The compounds of Examples 1-9, 11-14, 16-34, 36-45 and 47-59 in the following tables were produced according to the methods described in the above-mentioned Examples, or methods analogous thereto.

TABLE 1-1

| EXAMPLE | IUPAC NAME | Structure | ADDITIVE | MS |
|---|---|---|---|---|
| 1 | (4-(1-methyl-2-(trifluoromethyl)-1H-benzimidazol-4-yl)phenyl)(morpholin-4-yl)methanone | 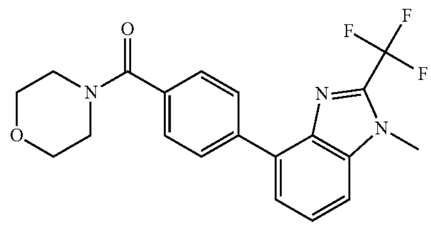 | | 390.1 |
| 2 | (4-(1-ethyl-2-(trifluoromethyl)-1H-benzimidazol-4-yl)phenyl)(morpholin-4-yl)methanone | 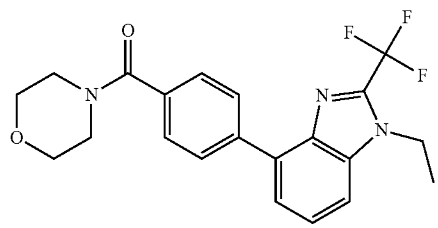 [SMILES: CCn1c(C(F)(F)F)nc2c(-c3ccc(C(=O)N4CCOCC4)cc3)cccc21] | | 404.0 |
| 3 | (4-(1-isopropyl-2-(trifluoromethyl)-1H-benzimidazol-4-yl)phenyl)(morpholin-4-yl)methanone | 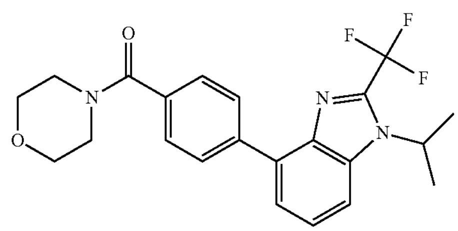 [SMILES: CC(C)n1c(C(F)(F)F)nc2c(-c3ccc(C(=O)N4CCOCC4)cc3)cccc21] | | 418.0 |
| 4 | (4-(1-ethyl-2-(trifluoromethyl)-1H-imidazo[4,5-c]pyridin-4-yl)phenyl)(morpholin-4-yl)methanone | 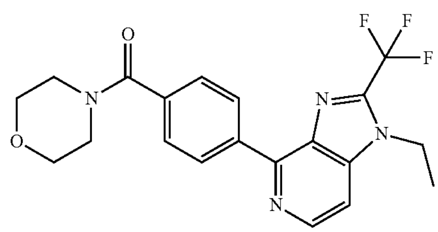 [SMILES: CCn1c(C(F)(F)F)nc2c(-c3ccc(C(=O)N4CCOCC4)cc3)nccc21] | | 405.1 |
| 5 | (4-(1-(difluoromethyl)-2-(trifluoromethyl)-1H-imidazo[4,5-c]pyridin-4-yl)phenyl)(morpholin-4-yl)methanone | 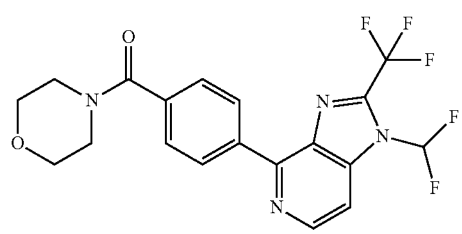 [SMILES: O=C(c1ccc(-c2nccc3c2nc(C(F)(F)F)n3C(F)F)cc1)N1CCOCC1] | | 427.0 |
| 6 | (4-(1-methyl-2-(trifluoromethyl)-1H-imidazo[4,5-c]pyridin-4-yl)phenyl)(morpholin-4-yl)methanone | 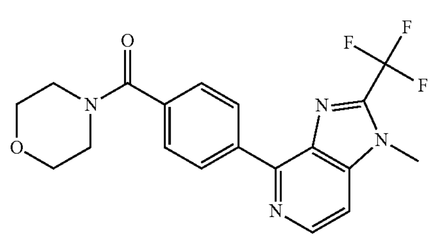 [SMILES: Cn1c(C(F)(F)F)nc2c(-c3ccc(C(=O)N4CCOCC4)cc3)nccc21] | | 391.0 |

TABLE 1-1-continued

| EXAMPLE | IUPAC NAME | Structure | ADDITIVE | MS |
|---|---|---|---|---|
| 7 | (4-(1-(2,2-difluoroethyl)-2-(trifluoromethyl)-1H-benzimidazol-4-yl)phenyl)(morpholin-4-yl)methanone | 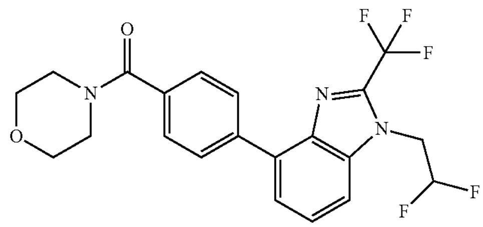 [SMILES: O=C(c1ccc(-c2cccc3c2nc(C(F)(F)F)n3CC(F)F)cc1)N1CCOCC1] | | 440.1 |

TABLE 1-2

| EXAMPLE | IUPAC NAME | Structure | ADDITIVE | MS |
|---|---|---|---|---|
| 8 | (4-(1-ethyl-2-(trifluoromethyl)-1H-imidazo[4,5-c]pyridin-4-yl)-2-fluorophenyl)(morpholin-4-yl)methanone | 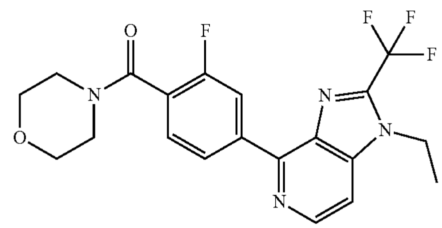 [SMILES: CCn1c(C(F)(F)F)nc2c(-c3ccc(C(=O)N4CCOCC4)c(F)c3)nccc21] | | 423.1 |
| 9 | (4-(1-ethyl-2-(trifluoromethyl)-1H-imidazo[4,5-c]pyridin-4-yl)-2-fluorophenyl)((2S)-2-methylmorpholin-4-yl)methanone | 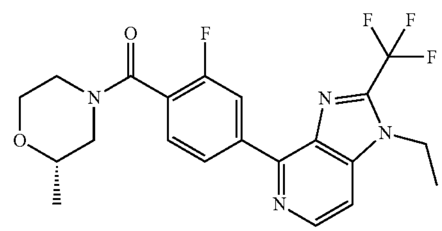 [SMILES: CCn1c(C(F)(F)F)nc2c(-c3ccc(C(=O)N4CCO[C@@H](C)C4)c(F)c3)nccc21] | | 437.1 |
| 10 | (4-(1-(2,2-difluoroethyl)-2-(trifluoromethyl)-1H-imidazo[4,5-c]pyridin-4-yl)-2-fluorophenyl)(morpholin-4-yl)methanone | 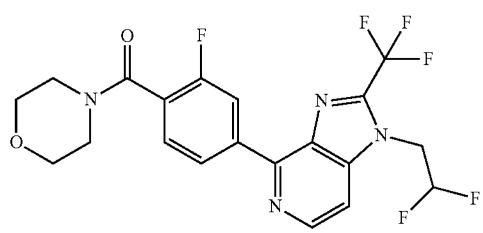 [SMILES: O=C(c1ccc(-c2nccc3c2nc(C(F)(F)F)n3CC(F)F)cc1F)N1CCOCC1] | | 459.1 |
| 11 | (2-fluoro-4-(1-methyl-2-(trifluoromethyl)-1H-benzimidazol-4-yl)phenyl)(2S)-2-methylmorpholin-4-yl)methanone | 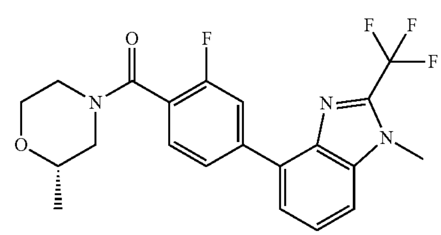 [SMILES: C[C@H]1CN(C(=O)c2ccc(-c3cccc4c3nc(C(F)(F)F)n4C)cc2F)CCO1] | | 422.1 |
| 12 | (2-fluoro-4-(1-methyl-2-(trifluoromethyl)-1H-benzimidazol-4-yl)phenyl)(morpholin-4-yl)methanone | 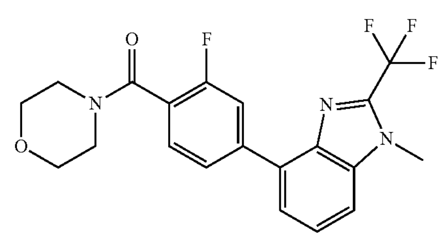 [SMILES: Cn1c(C(F)(F)F)nc2c(-c3ccc(C(=O)N4CCOCC4)c(F)c3)cccc21] | | 408.0 |

TABLE 1-2-continued

| EXAMPLE | IUPAC NAME | Structure | ADDITIVE | MS |
|---|---|---|---|---|
| 13 | (4-(1-(2,2-difluoroethyl)-2-(trifluoromethyl)-1H-benzimidazol-4-yl)phenyl)((2S)-2-methylmorpholin-4-yl)methanone | 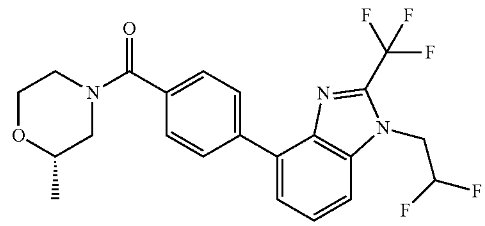 [SMILES: C[C@H]1CN(C(=O)c2ccc(-c3cccc4c3nc(C(F)(F)F)n4CC(F)F)cc2)CCO1] | | 454.1 |
| 14 | (4-(1-(2,2-difluoroethyl)-2-(trifluoromethyl)-1H-benzimidazol-4-yl)phenyl)(1,4-oxazepan-4-yl)methanone | 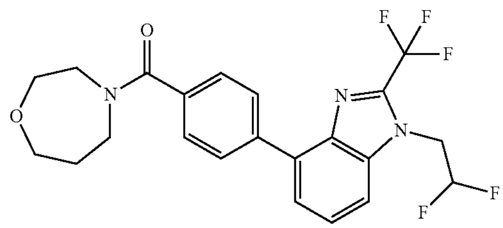 [SMILES: O=C(c1ccc(-c2cccc3c2nc(C(F)(F)F)n3CC(F)F)cc1)N1CCCOCC1] | | 454.1 |

TABLE 1-3

| EXAMPLE | IUPAC NAME | Structure | ADDITIVE | MS |
|---|---|---|---|---|
| 15 | (4-(1-(2,2-difluoroethyl)-2-(trifluoromethyl)-1H-imidazo[4,5-c]pyridin-4-yl)-2-fluorophenyl)(1,4-oxazepan-4-yl)methanone | 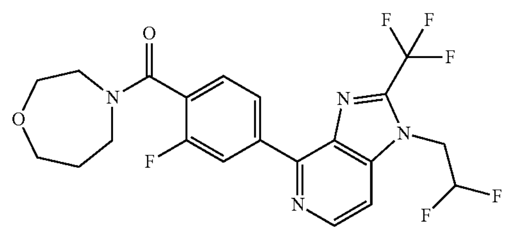 [SMILES: O=C(c1ccc(-c2nccc3c2nc(C(F)(F)F)n3CC(F)F)cc1F)N1CCCOCC1] | | 473.1 |
| 16 | (4-(1-(2,2-difluoroethyl)-2-(trifluoromethyl)-1H-benzimidazol-4-yl)phenyl)(2-(difluoromethyl)morpholin-4-yl)methanone | 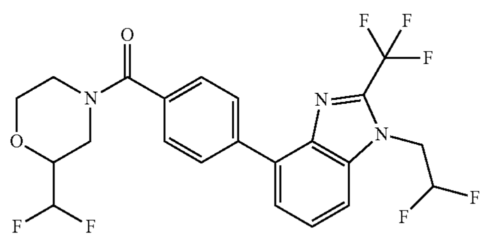 [SMILES: O=C(c1ccc(-c2cccc3c2nc(C(F)(F)F)n3CC(F)F)cc1)N1CCOC(C(F)F)C1] | | 490.1 |
| 17 | (4-(1-(2,2-difluoroethyl)-2-(trifluoromethyl)-1H-imidazo[4,5-c]pyridin-4-yl)-2-fluorophenyl)((2S)-2-methylmorpholin-4-yl)methanone | 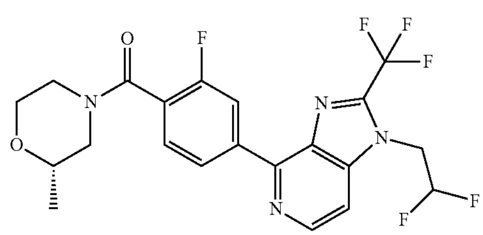 [SMILES: C[C@H]1CN(C(=O)c2ccc(-c3nccc4c3nc(C(F)(F)F)n4CC(F)F)cc2F)CCO1] | | 473.0 |
| 18 | (4-(4-(morpholin-4-ylcarbonyl)phenyl)-2-(trifluoromethyl)-1H-benzimidazol-1-yl)acetonitrile | 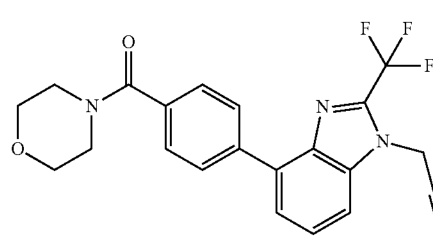 | | 415.1 |

TABLE 1-3-continued

| EXAMPLE | IUPAC NAME | Structure | ADDITIVE | MS |
|---|---|---|---|---|
| 19 | N-(2-cyanoethyl)-4-(1-(2,2-difluoroethyl)-2-(trifluoromethyl)-1H-imidazo[4,5-c]pyridin-4-yl)-2-fluoro-N-methylbenzamide | 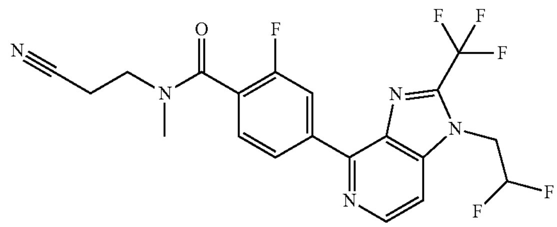 [SMILES: CN(CCC#N)C(=O)c1ccc(-c2nccc3c2nc(C(F)(F)F)n3CC(F)F)cc1F] | | 456.0 |
| 20 | (2-fluoro-4-(1-(2-methoxyethyl)-2-(trifluoromethyl)-1H-imidazo[4,5-c]pyridin-4-yl)phenyl)(morpholin-4-yl)methanone | 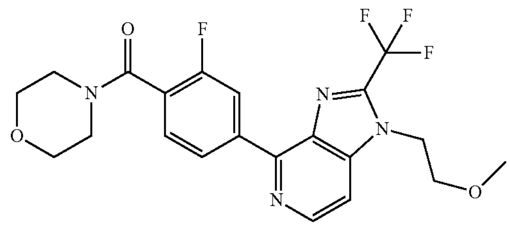 [SMILES: COCCn1c(C(F)(F)F)nc2c(-c3ccc(C(=O)N4CCOCC4)c(F)c3)nccc21] | | 453.1 |
| 21 | N-(2-cyanoethyl)-4-(1-(2,2-difluoroethyl)-2-(trifluoromethyl)-1H-benzimidazol-4-yl)-N-methylbenzamide | 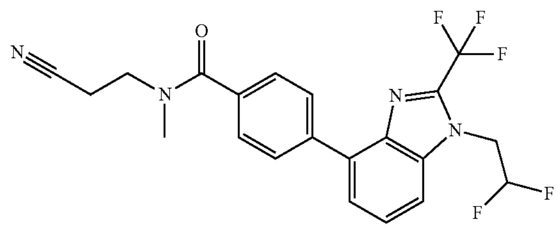 [SMILES: CN(CCC#N)C(=O)c1ccc(-c2cccc3c2nc(C(F)(F)F)n3CC(F)F)cc1] | | 437.1 |

TABLE 1-4

| EXAMPLE | IUPAC NAME | Structure | ADDITIVE | MS |
|---|---|---|---|---|
| 22 | (4-(1-(2,2-difluoroethyl)-2-(trifluoromethyl)-1H-benzimidazol-4-yl)phenyl)(2-(difluoromethyl)morpholin-4-yl)methanone optical isomer (retention time: shorter) | 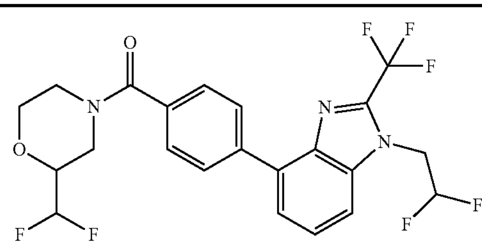 | | 490.1 |
| 23 | (4-(1-(2,2-difluoroethyl)-2-(trifluoromethyl)-1H-benzimidazol-4-yl)phenyl)(2-(difluoromethyl)morpholin-4-yl)methanone optical isomer (retention time: longer) | 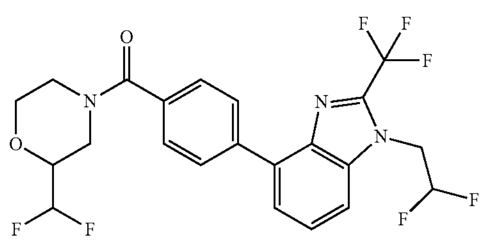 [SMILES: O=C(c1ccc(-c2cccc3c2nc(C(F)(F)F)n3CC(F)F)cc1)N1CCOC(C(F)F)C1] | | 490.1 |
| 24 | azetidin-1-yl(4-(1-(2,2-difluoroethyl)-2-(trifluoromethyl)-1H-imidazo[4,5-c]pyridin-4-yl)-2-fluorophenyl)methanone | 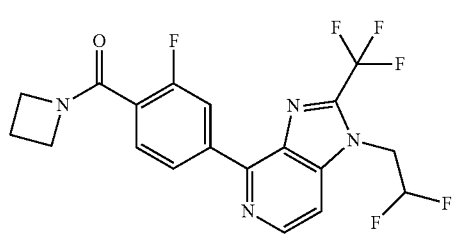 [SMILES: O=C(c1ccc(-c2nccc3c2nc(C(F)(F)F)n3CC(F)F)cc1F)N1CCC1] | | 429.2 |

TABLE 1-4-continued

| EXAMPLE | IUPAC NAME | Structure | ADDITIVE | MS |
|---|---|---|---|---|
| 25 | (2-fluoro-4-(1-(2,2,2-trifluoroethyl)-2-(trifluoromethyl)-1H-imidazo[4,5-c]pyridin-4-yl)phenyl)(morpholin-4-yl)methanone | 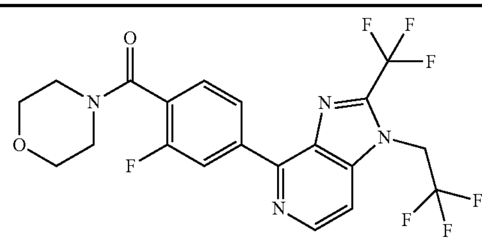 | | 477.1 |
| 26 | (3,3-difluoroazetidin-1-yl)(4-(1-(2,2-difluoroethyl)-2-(trifluoromethyl)-1H-imidazo[4,5-c]pyridin-4-yl)-2-fluorophenyl)methanone | 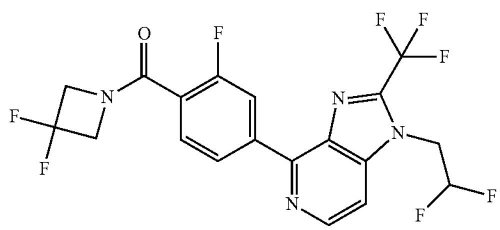 [SMILES: O=C(c1ccc(-c2nccc3c2nc(C(F)(F)F)n3CC(F)F)cc1F)N1CC(F)(F)C1] | | 465.0 |
| 27 | 4-(1-(2,2-difluoroethyl)-2-(trifluoromethyl)-1H-benzimidazol-4-yl)-N-((3S)-tetrahydro-2H-pyran-3-yl)benzamide | 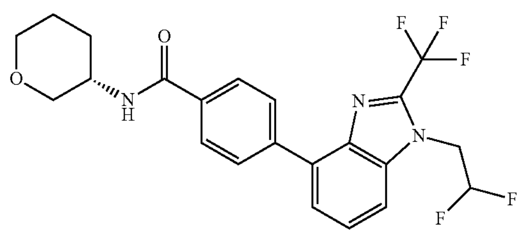 | | 454.1 |
| 28 | 4-(1-(2,2-difluoroethyl)-2-(trifluoromethyl)-1H-imidazo[4,5-c]pyridin-4-yl)-2-fluoro-N-methyl-N-(tetrahydro-2H-pyran-4-yl)benzamide | 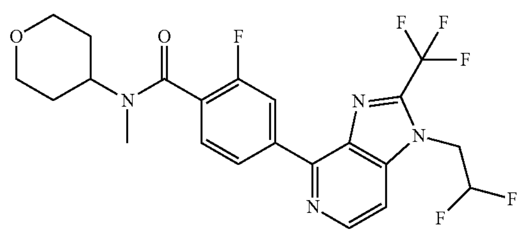 [SMILES: CN(C(=O)c1ccc(-c2nccc3c2nc(C(F)(F)F)n3CC(F)F)cc1F)C1CCOCC1] | | 487.0 |

TABLE 1-5

| EXAMPLE | IUPAC NAME | Structure | ADDITIVE | MS |
|---|---|---|---|---|
| 29 | (4-(1-(2,2-difluoroethyl)-2-(trifluoromethyl)-1H-benzimidazol-4-yl)phenyl)(6,6-difluoro-1,4-oxazepan-4-yl)methanone | 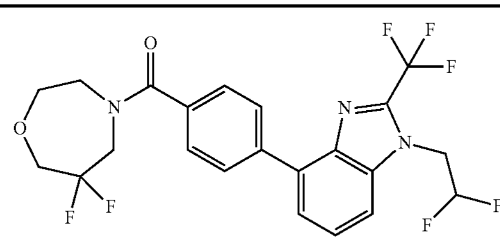 | | 490.1 |
| 30 | N-(2-cyanoethyl)-4-(1-(2,2-difluoroethyl)-2-(trifluoromethyl)-1H-imidazo[4,5-c]pyridin-4-yl)-2-fluoro-N-methylbenzamide | 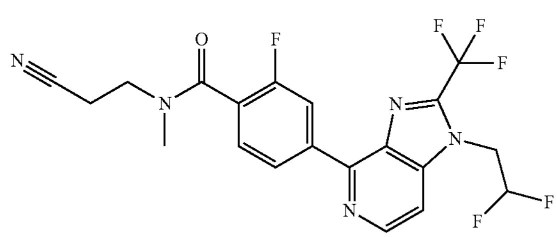 [SMILES: CN(CCC#N)C(=O)c1ccc(-c2nccc3c2nc(C(F)(F)F)n3CC(F)F)cc1F] | HCl | 456.0 |

TABLE 1-5-continued

| EXAMPLE | IUPAC NAME | Structure | ADDITIVE | MS |
|---|---|---|---|---|
| 31 | 4-(1-(2,2-difluoroethyl)-2-(trifluoromethyl)-1H-benzimidazol-4-yl)-N-(tetrahydro-2H-pyran-4-yl)benzamide | 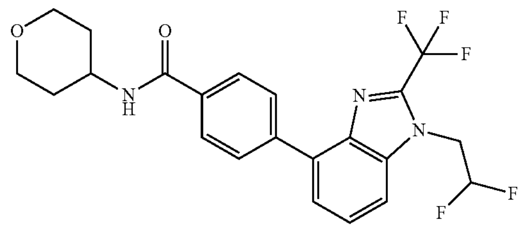 [SMILES: O=C(NC1CCOCC1)c1ccc(-c2cccc3c2nc(C(F)(F)F)n3CC(F)F)cc1] | | 454.0 |
| 32 | 4-(1-(2,2-difluoroethyl)-2-(trifluoromethyl)-1H-benzimidazol-4-yl)-N-((3R)-tetrahydro-2H-pyran-3-yl)benzamide | 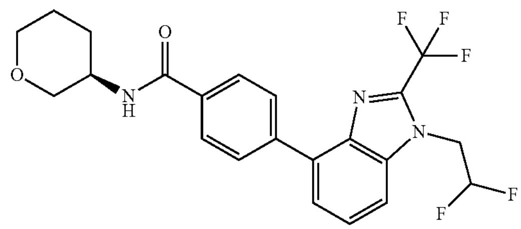 [SMILES: O=C(N[C@@H]1CCCOC1)c1ccc(-c2cccc3c2nc(C(F)(F)F)n3CC(F)F)cc1] | | 454.1 |
| 33 | N-(cyclopropylmethyl)-4-(1-(2,2-difluoroethyl)-2-(trifluoromethyl)-1H-imidazo[4,5-c]pyridin-4-yl)-2-fluorobenzamide | 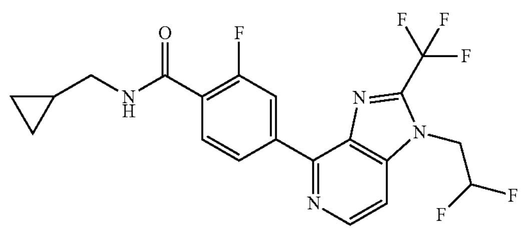 [SMILES: O=C(NCC1CC1)c1ccc(-c2nccc3c2nc(C(F)(F)F)n3CC(F)F)cc1F] | | 443.1 |
| 34 | (4-(1-(2,2-difluoroethyl)-2-(trifluoromethyl)-1H-imidazo[4,5-c]pyridin-4-yl)-2-fluorophenyl)(6,6-difluoro-1,4-oxazepan-4-yl)methanone | 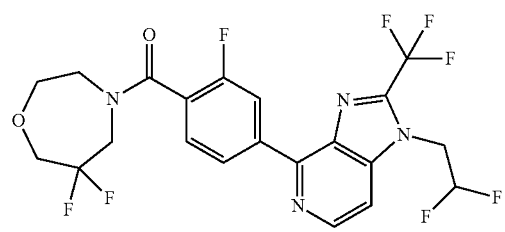 [SMILES: O=C(c1ccc(-c2nccc3c2nc(C(F)(F)F)n3CC(F)F)cc1F)N1CCOCC(F)(F)C1] | | 509.1 |
| 35 | (5-(1-(2,2-difluoroethyl)-2-(trifluoromethyl)-1H-benzimidazol-4-yl)-3-fluoropyridin-2-yl)(morpholin-4-yl)methanone | 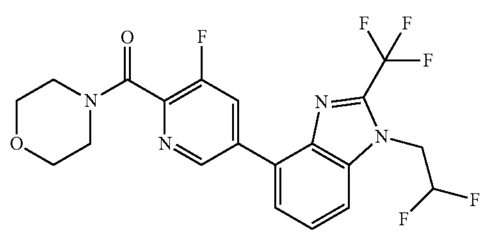 [SMILES: O=C(c1ncc(-c2cccc3c2nc(C(F)(F)F)n3CC(F)F)cc1F)N1CCOCC1] | | 459.1 |

TABLE 1-6

| EXAMPLE | IUPAC NAME | Structure | ADDITIVE | MS |
|---|---|---|---|---|
| 36 | (4-(1-(2,2-difluoroethyl)-5-fluoro-2-(trifluoromethyl)-1H-benzimidazol-4-yl)phenyl)(morpholin-4-yl)methanone | 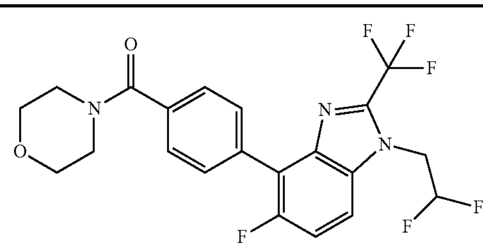 | | 458.1 |

TABLE 1-6-continued

| EXAMPLE | IUPAC NAME | Structure | ADDITIVE | MS |
|---|---|---|---|---|
| 37 | (4-(1-(2,2-difluoroethyl)-2-(trifluoromethyl)-1H-imidazo[4,5-c]pyridin-4-yl)-2-fluorophenyl)((3R)-3-methoxypyrrolidin-1-yl)methanone | 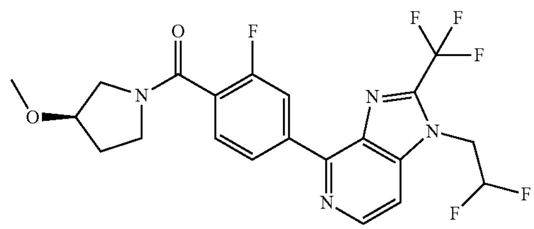 [SMILES: CO[C@@H]1CCN(C(=O)c2ccc(-c3nccc4c3nc(C(F)(F)F)n4CC(F)F)cc2F)C1] | | 473.1 |
| 38 | (4-(1-(2,2-difluoroethyl)-6-methyl-2-(trifluoromethyl)-1H-imidazo[4,5-c]pyridin-4-yl)-2-fluorophenyl)(6,6-difluoro-1,4-oxazepan-4-yl)methanone | 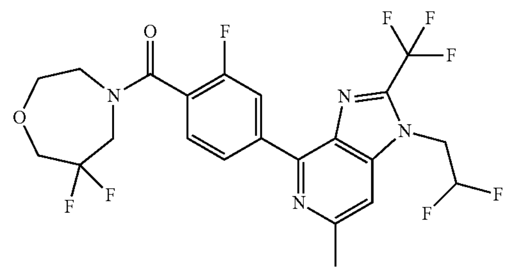 [SMILES: Cc1cc2c(nc(C(F)(F)F)n2CC(F)F)c(-c2ccc(C(=O)N3CCOCC(F)(F)C3)c(F)c2)n1] | | 523.1 |
| 39 | (5-(1-(2,2-difluoroethyl)-2-(trifluoromethyl)-1H-benzimidazol-4-yl)pyridin-2-yl)(6,6-difluoro-1,4-oxazepan-4-yl)methanone | 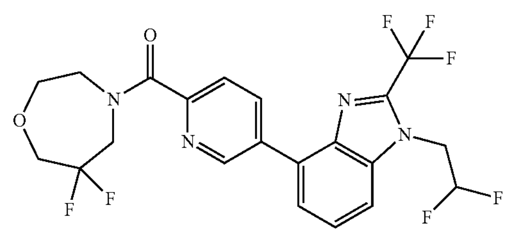 [SMILES: O=C(c1ccc(-c2cccc3c2nc(C(F)(F)F)n3CC(F)F)cn1)N1CCOCC(F)(F)C1] | | 491.1 |
| 40 | (4-(1-(2,2-difluoroethyl)-6-methyl-2-(trifluoromethyl)-1H-imidazo[4,5-c]pyridin-4-yl)-2-fluorophenyl)(morpholin-4-yl)methanone | 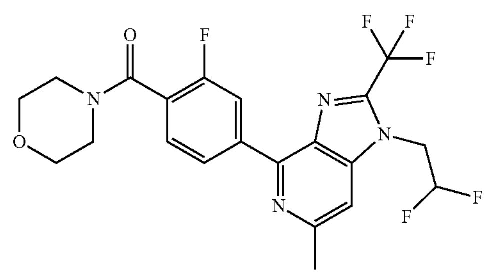 [SMILES: Cc1cc2c(nc(C(F)(F)F)n2CC(F)F)c(-c2ccc(C(=O)N3CCOCC3)c(F)c2)n1] | | 473.1 |
| 41 | (4-(1-(2,2-difluoroethyl)-6-methyl-2-(trifluoromethyl)-1H-imidazo[4,5-c]pyridin-4-yl)-2-fluorophenyl)(1,4-oxazepan-4-yl)methanone | 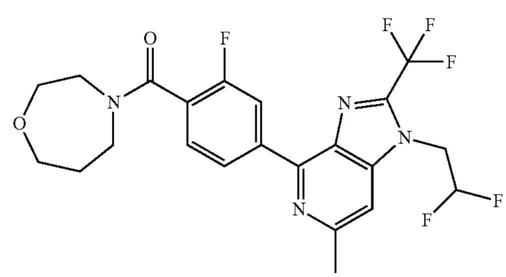 [SMILES: Cc1cc2c(nc(C(F)(F)F)n2CC(F)F)c(-c2ccc(C(=O)N3CCCOCC3)c(F)c2)n1] | | 487.1 |
| 42 | (4-(1-(2,2-difluoroethyl)-2-(trifluoromethyl)-1H-imidazo[4,5-c]pyridin-4-yl)-2,3-difluorophenyl)(morpholin-4-yl)methanone | 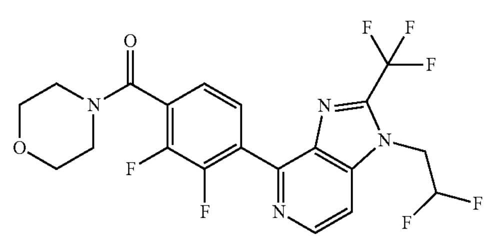 [SMILES: O=C(c1ccc(-c2nccc3c2nc(C(F)(F)F)n3CC(F)F)c(F)c1F)N1CCOCC1] | | 477.1 |

TABLE 1-7

| EXAMPLE | IUPAC NAME | Structure | ADDITIVE | MS |
|---|---|---|---|---|
| 43 | (4-(1-(2,2-difluoroethyl)-2-(trifluoromethyl)-1H-imidazo[4,5-c]pyridin-4-yl)-2-fluorophenyl)((3S)-3-methoxypyrrolidin-1-yl)methanone | 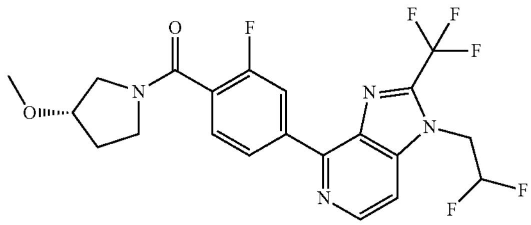 [SMILES: CO[C@H]1CCN(C(=O)c2ccc(-c3nccc4c3nc(C(F)(F)F)n4CC(F)F)cc2F)C1] | | 473.1 |
| 44 | (4-(1-(2,2-difluoroethyl)-2-(trifluoromethyl)-1H-imidazo[4,5-c]pyridin-4-yl)-2-fluorophenyl)((2R)-2-methylmorpholin-4-yl)methanone | 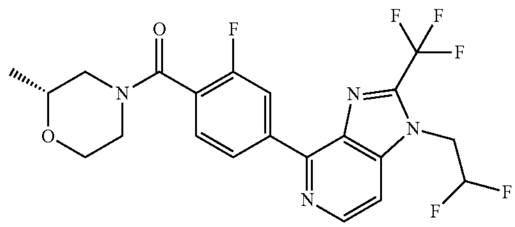 [SMILES: C[C@@H]1CN(C(=O)c2ccc(-c3nccc4c3nc(C(F)(F)F)n4CC(F)F)cc2F)CCO1] | | 473.0 |
| 45 | (5-(1-(2,2-difluoroethyl)-5-methyl-2-(trifluoromethyl)-1H-benzimidazol-4-yl)-3-fluoropyridin-2-yl)(morpholin-4-yl)methanone | 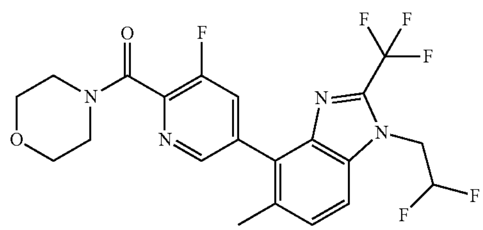 [SMILES: Cc1ccc2c(nc(C(F)(F)F)n2CC(F)F)c1-c1cnc(C(=O)N2CCOCC2)c(F)c1] | | 473.1 |
| 46 | (6-(1-(2,2-difluoroethyl)-2-(trifluoromethyl)-1H-benzimidazol-4-yl)pyridin-3-yl)(6,6-difluoro-1,4-oxazepan-4-yl)methanone | 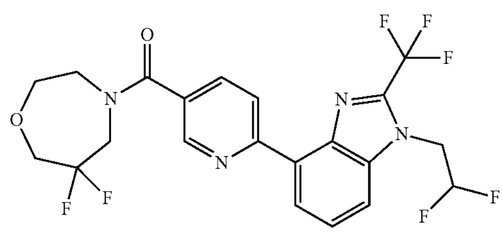 | | 491.1 |
| 47 | (6-(1-(2,2-difluoroethyl)-2-(trifluoromethyl)-1H-benzimidazol-4-yl)pyridin-3-yl)(morpholin-4-yl)methanone | 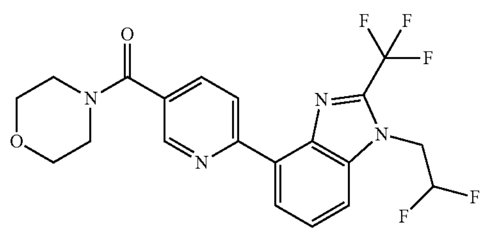 [SMILES: O=C(c1ccc(-c2cccc3c2nc(C(F)(F)F)n3CC(F)F)nc1)N1CCOCC1] | | 441.1 |
| 48 | (4-(1-(2,2-difluoroethyl)-2-(trifluoromethyl)-1H-imidazo[4,5-c]pyridin-4-yl)-2-fluorophenyl)(5-oxa-8-azaspiro[2.6]non-8-yl)methanone | 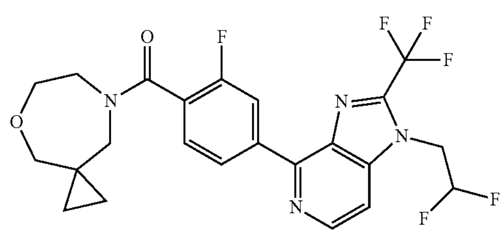 [SMILES: O=C(c1ccc(-c2nccc3c2nc(C(F)(F)F)n3CC(F)F)cc1F)N1CCOCC2(CC2)C1] | | 499.0 |

TABLE 1-7-continued

| EXAMPLE | IUPAC NAME | Structure | ADDITIVE | MS |
|---|---|---|---|---|
| 49 | (5-(1-(2,2-difluoroethyl)-5-methyl-2-(trifluoromethyl)-1H-benzimidazol-4-yl)-3-fluoropyridin-2-yl)(6,6-difluoro-1,4-oxazepan-4-yl)methanone | 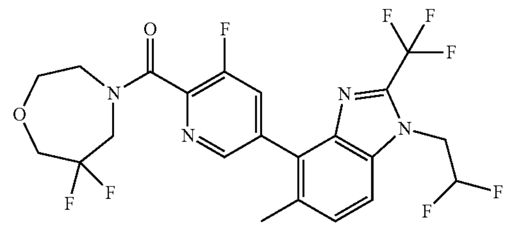 [SMILES: Cc1ccc2c(nc(C(F)(F)F)n2CC(F)F)c1-c1cnc(C(=O)N2CCOCC(F)(F)C2)c(F)c1] | | 523.1 |

TABLE 1-8

| EXAMPLE | IUPAC NAME | Structure | ADDITIVE | MS |
|---|---|---|---|---|
| 50 | (4-(1-(2,2-difluoroethyl)-2-(trifluoromethyl)-1H-imidazo[4,5-c]pyridin-4-yl)phenyl)(6,6-difluoro-1,4-oxazepan-4-yl)methanone | 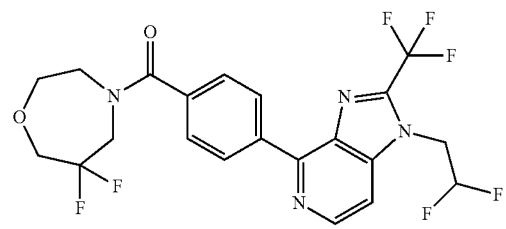 [SMILES: O=C(c1ccc(-c2nccc3c2nc(C(F)(F)F)n3CC(F)F)cc1)N1CCOCC(F)(F)C1] | | 491.1 |
| 51 | (4-(1-(2,2-difluoroethyl)-2-(trifluoromethyl)-1H-benzimidazol-4-yl)-3-fluorophenyl)(morpholin-4-yl)methanone | 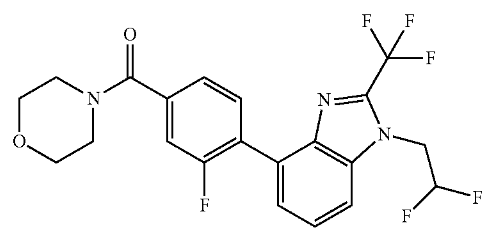 [SMILES: O=C(c1ccc(-c2cccc3c2nc(C(F)(F)F)n3CC(F)F)c(F)c1)N1CCOCC1] | | 458.1 |
| 52 | (4-(1-(2,2-difluoroethyl)-2-(trifluoromethyl)-1H-imidazo[4,5-c]pyridin-4-yl)-2-fluorophenyl)(4-methoxypiperidin-1-yl)methanone | 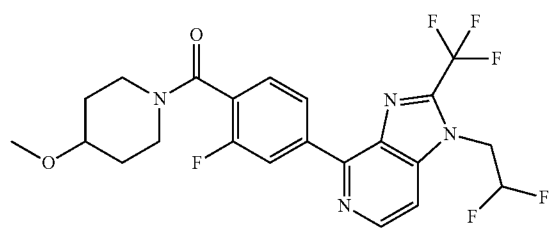 [SMILES: COC1CCN(C(=O)c2ccc(-c3nccc4c3nc(C(F)(F)F)n4CC(F)F)cc2F)CC1] | | 487.1 |
| 53 | (4-(1-(2,2-difluoroethyl)-2-(trifluoromethyl)-1H-imidazo[4,5-c]pyridin-4-yl)-3-fluorophenyl)(morpholin-4-yl)methanone | 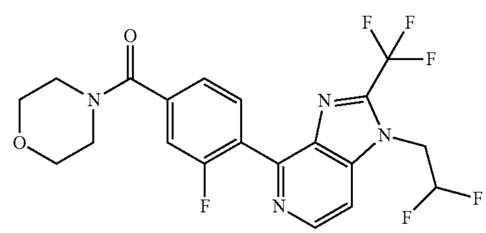 [SMILES: O=C(c1ccc(-c2nccc3c2nc(C(F)(F)F)n3CC(F)F)c(F)c1)N1CCOCC1] | | 458.9 |
| 54 | (4-(1-(2,2-difluoroethyl)-2-(trifluoromethyl)-1H-imidazo[4,5-c]pyridin-4-yl)-3-fluorophenyl)(morpholin-4-yl)methanone | 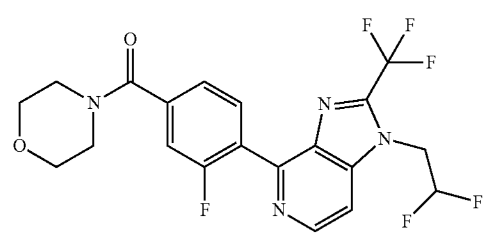 [SMILES: O=C(c1ccc(-c2nccc3c2nc(C(F)(F)F)n3CC(F)F)c(F)c1)N1CCOCC1] | HCl | 459.1 |

TABLE 1-8-continued

| EXAMPLE | IUPAC NAME | Structure | ADDITIVE | MS |
|---|---|---|---|---|
| 55 | (4-(1-(2,2-difluoroethyl)-2-(trifluoromethyl)-1H-imidazo[4,5-c]pyridin-4-yl)-2,3-difluorophenyl)(morpholin-4-yl)methanone | 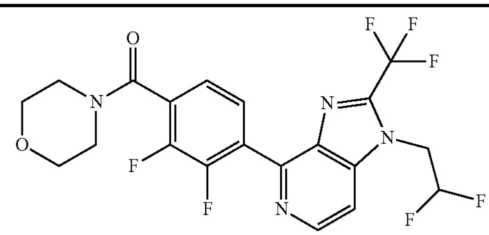 | HCl | 477.1 |
| 56 | (4-(1-(2,2-difluoroethyl)-2-(trifluoromethyl)-1H-imidazo[4,5-c]pyridin-4-yl)phenyl)(morpholin-4-yl)methanone | 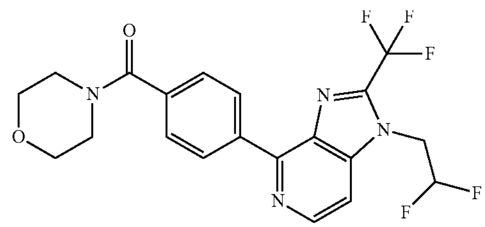 [SMILES: O=C(c1ccc(-c2nccc3c2nc(C(F)(F)F)n3CC(F)F)cc1)N1CCOCC1] | | 441.1 |

TABLE 9

| EXAMPLE | IUPAC NAME | Structure | ADDITIVE | MS |
|---|---|---|---|---|
| 57 | (4-(1-(2,2-difluoroethyl)-2-(trifluoromethyl)-1H-imidazo[4,5-c]pyridin-4-yl)-2-methoxyphenyl)(morpholin-4-yl)methanone | 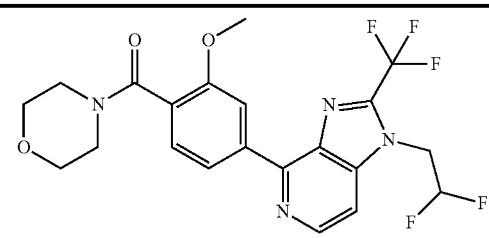 | | 471.1 |
| 58 | (4-(1-(2,2-difluoroethyl)-2-(trifluoromethyl)-1H-imidazo[4,5-c]pyridin-4-yl)-2-methoxyphenyl)(6,6-difluoro-1,4-oxazepan-4-yl)methanone | 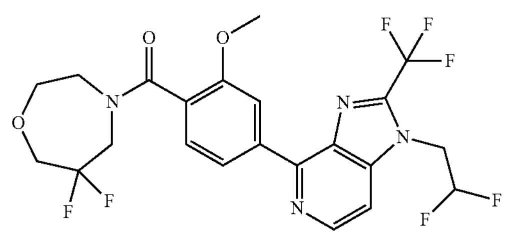 [SMILES: COc1cc(-c2nccc3c2nc(C(F)(F)F)n3CC(F)F)ccc1C(=O)N1CCOCC(F)(F)C1] | | 521.1 |
| 59 | (4-(1-(2,2-difluoroethyl)-2-(trifluoromethyl)-1H-imidazo[4,5-c]pyridin-4-yl)-2-fluorophenyl)(2,2-difluoromorpholin-4-yl)methanone | 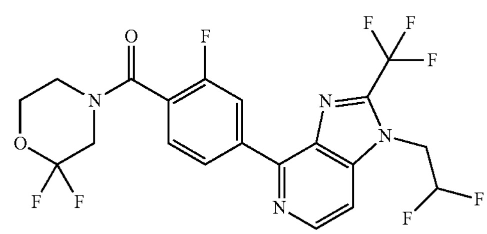 [SMILES: O=C(c1ccc(-c2nccc3c2nc(C(F)(F)F)n3CC(F)F)cc1F)N1CCOC(F)(F)C1] | | 494.8 |

In Examples 22 and 23, the optical isomer was obtained by resolving the compound of Example 16 with HPLC (column: CHIRALCEL OD(IK001), 50 mmID×500 mmL, Manufactured by Daicel Chemical Industries, mobile phase: hexane/ethanol=450/550). The compound having a shorter retention time was obtained as the compound of Example 22 by the resolution, whereas the compound having a longer retention time was obtained as the compound of Example 23 by the resolution.

Experimental Example 1 Measurement Method of AMPA Receptor Function-Enhancing Activity of Compound Using Calcium Influx as Index (1) Construction of Expression Gene Human GluR1 flip cDNA was amplified by PCR method using forward primer ACTGAATTCGCCAC-CATGCAGCACATTTTTGCCTTCTTCTGC (SEQ ID NO: 1) and reverse primer CCGCGGCCGCTTA-CAATCCCGTGGCTCCCAAG (SEQ ID NO: 2) artificially synthesized using human brain-derived cDNA (BD Bioscience) as a template. The amplified product was digested with restriction enzymes EcoRI, NotI (TAKARA SHUZO CO. LTD.) and incorporated into the same site of pcDNA3.1(+) (Invitrogen) to construct pcDNA3.1(+)/human GluR1 flip gene. Human stargazin cDNA was amplified by PCR method using forward primer GGTCTCGAGGCCAC-CATGGGGCTGTTTGATCGAGGTGTTCA (SEQ ID NO: 3) and reverse primer GTTGGATCCT-TATACGGGGGTGGTCCGGCGGTTGGCTGTG (SEQ ID NO: 4) artificially synthesized using human hippocampus cDNA as a template. The amplified product was digested with restriction enzymes XhoI, BamHI (TAKARA SHUZO CO. LTD.) and incorporated into the same site of pcDNA3.1 (−) (Invitrogen) to construct pcDNA3.1 Zeo(−)/human stargazing gene.

(2) Construction of GluR1 Flip/Stargazin Expressing Cell

CHO-K1 cells passaged in a culture medium (Ham's F12 medium (Invitrogen) added with 10% inactivated fetal bovine serum (Morgate) and penicillin, streptomycin (Invitrogen)) were detached using 0.05% trypsin and 0.53 mM EDTA (Invitrogen) diluted with D-PBS(−). The detached cells were suspended in a culture medium, and recovered by centrifugation at 1,000 rpm. The recovered cells were re-suspended in D-PBS(−) and added into 0.4 cm electroporation cuvette (BioRad). pcDNA3.1(+)/human GluR1 flip gene (5 µg) and pcDNA3.1 Zeo(−)/human stargazin gene (15 µg) were added, and introduced into CHO-K1 cells under the conditions of 950 µFd, 250 mV and using Gene Pulser II (BioRad). The introduced cells were cultured overnight in a culture medium. The next day, using a selection medium (culture medium added with zeocin (Invitrogen) at 250 µg/mL), the cells were plated in a 96 well plate at 250 cells/well. The clones showing drug resistance were selected, and GluR1 flip/stargazin expression clones were selected by an assay method shown below using calcium influx as an index.

(3) Measurement Method of AMPA Receptor Function-Enhancing Activity of Compound, Using Calcium Influx as an Index CHO-K1/GluR1 flip/stargazin-expressing cells were plated on a 384 well black bottom transparent plate, and cultured for 2 days in a $CO_2$ incubator (SANYO ELECTRIC Co. Ltd.) at 37° C. The medium of the cell plate was removed. A calcium indicator (Calcium5 Assay Kit, Molecular Devices) was diluted with an assay buffer (HBSS (Thermo Fisher Scientific), 0.1% BSA (Merck Millipoer) and 10 mM HEPES (Thermo Fisher Scientific)), and 1.25 mM probenecid (Dojindo Laboratories) was added thereto. The mixture prepared above was added at 30 µL/well (100 µL/well in case of 96 wells) to the well, and the well was left standing in 37° C., $CO_2$ incubator for 1 hr. The cell plate was set in CellLux (PerkinElmer), a mixture (15 µL) (50 µL/well in case of 96 wells) of 9 mM glutamic acid (final concentration 3 mM) diluted with an assay buffer and a test compound (test compound concentration 30 µM) was added thereto, and variation in the amount of fluorescence was measured for 3 min. The variation of fluorescence level of a well added with final concentration 3 mM of glutamic acid and 300 µM cyclothiazide (TOCRIS) was defined as 100%, the variation of fluorescence level of a well added with final concentration 3 mM of glutamic acid alone was defined as 0%, and the activity of the compound was calculated by the following formula.

activity (%)=$(X-C)/(T-C) \times 100$

T: variation of fluorescence level of well added with final concentration 3 mM of glutamic acid and 300 µM cyclothiazide C: variation of fluorescence level of well added with final concentration 3 mM of glutamic acid alone X: variation of fluorescence level of well added with test compound The results are shown in Table 2.

TABLE 2

| Example No. | hG1uR1 flip/30 µM (%) |
|---|---|
| 2 | 79.3 |
| 4 | 68.4 |
| 7 | 83.3 |
| 8 | 108.9 |
| 9 | 110.4 |
| 10 | 90.5 |
| 11 | 80.3 |
| 12 | 84.4 |
| 13 | 112.2 |
| 14 | 92.6 |
| 15 | 72 |
| 16 | 107.6 |
| 17 | 95.1 |
| 19 | 81 |
| 21 | 93.7 |
| 22 | 105.5 |
| 23 | 103 |
| 24 | 78.1 |
| 26 | 79.3 |
| 28 | 97.8 |
| 29 | 93 |
| 30 | 92.6 |
| 34 | 94.2 |
| 35 | 81.2 |
| 36 | 93.5 |
| 37 | 89.8 |
| 38 | 100.4 |
| 39 | 110.2 |
| 42 | 83.9 |
| 44 | 85.5 |
| 46 | 77 |
| 48 | 80.2 |
| 50 | 122.2 |
| 51 | 113 |
| 52 | 67.1 |
| 53 | 69 |

As shown in Table 2, the compound of the present invention induced cellular calcium influx in an AMPA receptor-expressing cells. That is to say the compound of the present invention has an AMPA receptor potentiator effect.

Experimental Example 2 Novel Object Recognition Test (1) Animals

Male Long Evans rats were supplied by Japan SLC, and used at 7-week-old in the experiments. After arrival to the vivarium, animals were allowed a minimum of 1 week for acclimation. They were housed under a 12:12-h light/dark cycle in a temperature- and humidity-controlled laboratory and allowed food and water ad libitum.

(2) Drug Administration

A test compound was suspended in 0.5% methylcellulose in distilled water and orally administered (p.o.). All test compounds were dosed in a volume of 2 mL/kg body weight for rats.

(3) Novel Object Recognition Test

Novel object recognition test is a test system utilizing the novel object preference characteristics of rodents. This novel object recognition test consists of two trials, "acquisition trial" and "retention trial", and, when an interval between these two trials is short, rodents spend a longer period for novel object exploration behaviors, and the preference dissipates as the interval gets longer. From this, the behavioral change in the novel object recognition test is considered to reflect the rodents' memory of the object during the acquisition trial. In this experimental example, the retention trial was carried out 48 hr after the acquisition trial. On the day before the test, for acclimation, Long-Evans rats were allowed to freely move about the test box (40× 40×50 cm) for 10 minutes. On the test day, the rats were acclimated to the test room for about 1 hr prior to the test. The test compound (Compound A (Example 10), Compound B (Example 35), 1 mg/kg) were orally administered to the rats twice 1 hr before the acquisition trial and 1 hr before the retention trial. For the acquisition trial, two identical objects (A1, A2) were placed in the test box. The rats were put in the test box for 3 min, and the duration contacting each object was measured. The retention trial was carried out 48 hr after the acquisition trial. For the retention trial, the familiar object (A3) used for the acquisition trial and the novel object (B) different shape from A3 were placed in the test box. The rats were put in the test box for 3 min. The duration contacting each object in the acquisition trial and the retention trial, and the novel object interaction (%) was calculated. The novel object interaction (%) was expressed as (the duration contacting the novel object)/[(the duration contacting the novel object)+(the duration contacting the familiar object)]×100(%) at mean±standard error. The results are shown in Table 3.

TABLE 3

| Novel Object Interaction (%) | Dose | |
|---|---|---|
| | 0 mg/kg | 1 mg/kg |
| Compound A (Example 10) | 51.08 ± 1.52 | 56.32 ± 1.56 |
| Compound B (Example 35) | 52.96 ± 2.03 | 61.28 ± 2.35 |

Preparation Example

| 1. capsule | |
|---|---|
| (1) compound obtained in Example 1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. Thereto is added the remaining (4) and the whole is sealed in a gelatin capsule.

| 2. tablet | |
|---|---|
| (1) compound obtained in Example 1 | 40 mg |
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. Thereto is added the remaining (4) and (5) and the mixture is compression formed into a tablet.

INDUSTRIAL APPLICABILITY

The compound of the present invention has an AMPA receptor potentiator effect, and is expected to be useful as an agent for the prophylaxis or treatment of depression, Alzheimer's disease, schizophrenia, attention deficit hyperactivity disorder (ADHD) and the like.

This application is based on patent application No. 2017-195906 filed on Oct. 6, 2017 in Japan, the contents of which are encompassed in full herein.

SEQUENCE LISTING FREE TEXT

35 [0247]

SEQ ID NO: 1 is a forward primer for GluR1 flip cDNA.
SEQ ID NO: 2 is a reverse primer for GluR1 flip cDNA.
SEQ ID NO: 3 is a forward primer for stargazin cDNA.
SEQ ID NO: 4 is a reverse primer for stargazin cDNA.

The invention claimed is:

1. A compound represented by the formula (I):

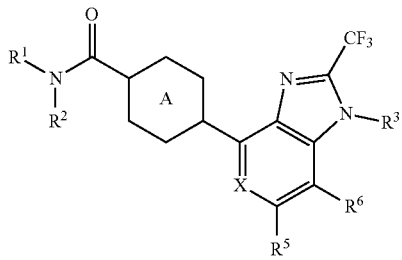

wherein $R^1$ and $R^2$ are each independently a hydrogen atom or a substituent, or $R^1$ and $R^2$ are bonded to each other to form, together with the adjacent nitrogen atom, a non-aromatic nitrogen-containing heterocycle that is unsubstituted or that is substituted with from one to three substituents independently selected from Substituent Group A, $R^3$ is a $C_{1-6}$ alkyl group that is unsubstituted or that is substituted with from one to five substituents independently selected from Substituent Group A, X is $CR^4$ or N, $R^4$, $R^5$ and $R^6$ are each independently a hydrogen atom, a halogen atom, a $C_{1-6}$ alkyl group that is unsubstituted or that is substituted with from one to five substituents independently selected from Substituent Group A or a $C_{1-6}$ alkoxy group that is unsubstituted or that is substituted with from one to five substituents independently selected from Substituent Group A, and Ring A is a 6-membered aromatic ring optionally further substituted by 1 to 4 substituents selected from (i) a halogen atom, (ii) a $C_{1-6}$ alkyl group and (iii) a $C_{1-6}$ alkoxy group, or a salt thereof, wherein Substituent Group A is the group consisting of:
(1) a halogen atom,
(2) a nitro group,
(3) a cyano group,
(4) an oxo group,
(5) a hydroxy group,
(6) a $C_{1-6}$ alkoxy group,
(7) a $C_{6-14}$ aryloxy group,
(8) a $C_{7-16}$ aralkyloxy group,
(9) a 5- to 14-membered aromatic heterocyclyloxy group,
(10) a 3- to 14-membered non-aromatic heterocyclyloxy group,
(11) a $C_{1-6}$ alkyl-carbonyloxy group,
(12) a $C_{6-14}$ aryl-carbonyloxy group,
(13) a $C_{1-6}$ alkoxy-carbonyloxy group,
(14) a mono- or di-$C_{1-6}$ alkyl-carbamoyloxy group,
(15) a $C_{6-14}$ aryl-carbamoyloxy group,
(16) a 5- to 14-membered aromatic heterocyclylcarbonyloxy group,
(17) a 3- to 14-membered non-aromatic heterocyclylcarbonyloxy group,
(18) an $C_{1-6}$ alkylsulfonyloxy group,
(19) a $C_{6-14}$ arylsulfonyloxy group,
(20) an $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an $C_{1-6}$ alkyl-carbonyl group,
(26) a $C_{6-14}$ aryl-carbonyl group,
(27) a 5- to 14-membered aromatic heterocyclylcarbonyl group,

(28) a 3- to 14-membered non-aromatic heterocyclylcarbonyl group,
(29) a $C_{1-6}$ alkoxy-carbonyl group,
(30) a $C_{6-14}$ aryloxy-carbonyl group,
(31) a $C_{7-16}$ aralkyloxy-carbonyl group,
(32) a carbamoyl group,
(33) a thiocarbamoyl group,
(34) a mono- or di-$C_{1-6}$ alkyl-carbamoyl group,
(35) a $C_{6-14}$ aryl-carbamoyl group,
(36) a 5- to 14-membered aromatic heterocyclylcarbamoyl group,
(37) a 3- to 14-membered non-aromatic heterocyclylcarbamoyl group,
(38) a $C_{1-6}$ alkylsulfonyl group,
(39) a $C_{6-14}$ arylsulfonyl group,
(40) a 5- to 14-membered aromatic heterocyclylsulfonyl group,
(41) a $C_{1-6}$ alkylsulfinyl group,
(42) a $C_{6-14}$ arylsulfinyl group,
(43) a 5- to 14-membered aromatic heterocyclylsulfinyl group,
(44) an amino group,
(45) a mono- or di-$C_{1-6}$ alkylamino group,
(46) a mono- or di-$C_{6-14}$ arylamino group,
(47) a 5- to 14-membered aromatic heterocyclylamino group,
(48) a $C_{7-16}$ aralkylamino group,
(49) a formylamino group,
(50) a $C_{1-6}$ alkyl-carbonylamino group,
(51) a ($C_{1-6}$ alkyl)($C_{1-6}$ alkyl-carbonyl) amino group,
(52) a $C_{6-14}$ aryl-carbonylamino group,
(53) a $C_{1-6}$ alkoxy-carbonylamino group,
(54) a $C_{7-16}$ aralkyloxy-carbonylamino group,
(55) a $C_{1-6}$ alkylsulfonylamino group,
(56) a $C_{6-14}$ arylsulfonylamino group,
(57) a $C_{1-6}$ alkyl group optionally substituted by 1 to 3 halogen atoms,
(58) a C2-6 alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

2. The compound or salt according to claim 1, wherein $R^1$ and $R^2$ are each independently
(1) a hydrogen atom,
(2) a $C_{1-6}$ alkyl group optionally substituted by 1 to 3 substituents selected from
(a) a cyano group, and
(b) a $C_{3-10}$ cycloalkyl group, or
(3) a 3- to 14-membered non-aromatic heterocyclic group, or
$R^1$ and $R^2$ are bonded to each other to form, together with the adjacent nitrogen atom, a 3- to 14-membered non-aromatic nitrogen-containing heterocycle optionally further substituted by 1 to 3 substituents selected from
(a) a halogen atom,
(b) a $C_{1-6}$ alkyl group optionally substituted by 1 to 3 halogen atoms, and
(c) a $C_{1-6}$ alkoxy group;
$R^3$ is a $C_{1-6}$ alkyl group optionally substituted by 1 to 3 substituents selected from
(a) a halogen atom,
(b) a cyano group, and
(c) a $C_{1-6}$ alkoxy group;
X is $CR^4$ or N;
$R^4$ is
(1) a hydrogen atom,
(2) a halogen atom, or
(3) a $C_{1-6}$ alkyl group;
$R^5$ is
(1) a hydrogen atom, or
(2) a $C_{1-6}$ alkyl group;
$R^6$ is a hydrogen atom; and
Ring A is
(1) a benzene ring optionally further substituted by 1 to 4 substituents selected from (i) a halogen atom, and (ii) a $C_{1-6}$ alkoxy group, or
(2) a pyridine ring optionally further substituted by 1 to 4 halogen atoms.

3. The compound or salt according to claim 1, wherein $R^1$ and $R^2$ are each independently
(1) a hydrogen atom,
(2) a $C_{1-6}$ alkyl group optionally substituted by 1 to 3 substituents selected from
(a) a cyano group, and
(b) a $C_{3-6}$ cycloalkyl group, or
(3) a tetrahydropyranyl group, or
$R^1$ and $R^2$ are bonded to each other to form, together with the adjacent nitrogen atom,
(1) a morpholine ring optionally further substituted by 1 to 3 substituents selected from
(a) a halogen atom, and
(b) a $C_{1-6}$ alkyl group optionally substituted by 1 to 3 halogen atoms,
(2) an oxazepane ring optionally further substituted by 1 to 3 halogen atoms,
(3) an azetidine ring optionally further substituted by 1 to 3 halogen atoms,
(4) a pyrrolidine ring optionally further substituted by 1 to 3 $C_{1-6}$ alkoxy groups,
(5) a piperidine ring optionally further substituted by 1 to 3 $C_{1-6}$ alkoxy groups, or
(6) a 5-oxa-8-azaspiro[2.6]nonane ring;
$R^3$ is a $C_{1-6}$ alkyl group optionally substituted by 1 to 3 substituents selected from
(a) a halogen atom,
(b) a cyano group, and
(c) a $C_{1-6}$ alkoxy group;
X is $CR^4$ or N;
$R^4$ is
(1) a hydrogen atom,
(2) a halogen atom, or
(3) a $C_{1-6}$ alkyl group;
$R^5$ is
(1) a hydrogen atom, or
(2) a $C_{1-6}$ alkyl group;
$R^6$ is a hydrogen atom; and
Ring A is
(1) a benzene ring optionally further substituted by 1 to 4 substituents selected from (i) a halogen atom, and (ii) a $C_{1-6}$ alkoxy group, or
(2) a pyridine ring optionally further substituted by 1 to 4 halogen atoms.

4. The compound or salt according to claim 1, wherein $R^1$ and $R^2$ are bonded to each other to form, together with the adjacent nitrogen atom,
(1) a morpholine ring, or
(2) an oxazepane ring optionally further substituted by 1 to 3 halogen atoms;
$R^3$ is a $C_{1-6}$ alkyl group substituted by 1 to 3 halogen atoms;
X is CH or N;
$R^5$ is a hydrogen atom;
$R^6$ is a hydrogen atom; and Ring A is
(1) a benzene ring optionally further substituted by 1 or 2 halogen atoms, or
(2) a pyridine ring optionally further substituted by 1 or 2 halogen atoms.

5. The compound or salt according to claim 1, wherein $R^1$ and $R^2$ are bonded to each other to form, together with the adjacent nitrogen atom,
(1) a morpholine ring, or
(2) an oxazepane ring;
$R^3$ is a $C_{1-6}$ alkyl group substituted by two halogen atoms;
X is CH or N;
$R^5$ is a hydrogen atom;
$R^6$ is a hydrogen atom; and
Ring A is
(1) a benzene ring optionally further substituted by one halogen atom, or
(2) a pyridine ring optionally further substituted by one halogen atom.

6. (4-(1-(2,2-Difluoroethyl)-2-(trifluoromethyl)-1 H-imidazo[4,5-c]pyridin-4-yl)-2-fluorophenyl)(morpholin-4-yl)methanone, or a salt thereof.

7. (4-(1-(2,2-Difluoroethyl)-2-(trifluoromethyl)-1 H-imidazo[4,5-c]pyridin-4-yl)-2-fluorophenyl)(1,4-oxazepan-4-yl)methanone, or a salt thereof.

8. (5-(1-(2,2-Difluoroethyl)-2-(trifluoromethyl)-1 H-benzimidazol-4-yl)-3-fluoropyridin-2-yl)(morpholin-4-yl)methanone, or a salt thereof.

9. A pharmaceutical composition comprising the compound or salt according to claim 1 and a pharmacologically acceptable carrier.

* * * * *

UNITED STATES PATENT AND TRADEMARK OFFICE
CERTIFICATE OF CORRECTION

PATENT NO. : 11,447,488 B2  
APPLICATION NO. : 16/753630  
DATED : September 20, 2022  
INVENTOR(S) : Tomoaki Hasui et al.

Page 1 of 2

It is certified that error appears in the above-identified patent and that said Letters Patent is hereby corrected as shown below:

In the Specification

Column 1, Lines 44-45, "treatment of psychiatric diseases, neurodegenerative disease, memory disorders, sleep disorder," should read --treatment of psychiatric diseases, neurodegenerative diseases, memory disorders, sleep disorders,--.

Column 28, Line 52, "and the like, and the like" should read --and the like--.

Column 28, Line 56, "and the like, and the like" should read --and the like--.

Column 28, Lines 62-63, "and the like, and the like" should read --and the like--.

Column 28, Line 66, "and the like, and the like" should read --and the like--.

Column 29, Line 4, "and the like, and the like" should read --and the like--.

Column 29, Line 12, "and the like, and the like" should read --and the like--.

Column 30, Line 55, "and the like, and the like" should read --and the like--.

Column 35, Line 8, "Example" should read --Examples--.

Column 41, Line 50, "mice, rats, hamster, rabbits," should read --mice, rats, hamsters, rabbits,--.

Column 42, Line 42, "disorder" should read --disorders--.

Column 43, Line 42, "referred to as concomitant drug" should read --referred to as a concomitant drug--.

Column 43, Line 61, "hydrocloride" should read --hydrochloride--.

Signed and Sealed this  
Twenty-fifth Day of April, 2023

Katherine Kelly Vidal  
*Director of the United States Patent and Trademark Office*

CERTIFICATE OF CORRECTION (continued)
U.S. Pat. No. 11,447,488 B2

In the Claims

Claim 2, Column 81, Line 40, "C2-6" should read as --$C_{2-6}$--.

Claim 6, Column 83, Lines 20-22, "(4-(1-(2,2-Difluoroethyl)-2-(trifluoromethyl)-1 H-imidazo[4,5-c]pyridin-4-yl)-2-fluorophenyl)(morpholin-4-yl)methanone," should read as --(4-(1-(2,2-Difluoroethyl)-2-(trifluoromethyl)-1H-imidazo[4,5-c]pyridin-4-yl)-2-fluorophenyl)(morpholin-4-yl)methanone,--.

Claim 7, Column 83, Lines 23-25, "(4-(1-(2,2-Difluoroethyl)-2-(trifluoromethyl)-1 H-imidazo[4,5-c]pyridin-4-yl)-2-fluorophenyl)(1,4-oxazepan-4-yl)methanone," should read as --"(4-(1-(2,2-Difluoroethyl)-2-(trifluoromethyl)-1H-imidazo[4,5-c]pyridin-4-yl)-2-fluorophenyl)(1,4-oxazepan-4-yl)methanone,--.

Claim 8, Column 83, Lines 26-28, "(5-(1-(2,2-Difluoroethyl)-2-(trifluoromethyl)-1 H-benzimidazol-4-yl)-3-fluoropyridin-2-yl)(morpholin-4-yl)methanone," should read as --(5-(1-(2,2-Difluoroethyl)-2-(trifluoromethyl)-1H-benzimidazol-4-yl)-3-fluoropyridin-2-yl)(morpholin-4-yl)methanone,--.